United States Patent
Lazarev et al.

(10) Patent No.: US 11,751,828 B2
(45) Date of Patent: *Sep. 12, 2023

(54) DIFFRACTOMETER-BASED GLOBAL IN SITU DIAGNOSTIC SYSTEM

(71) Applicant: EosDx Inc., Mountain View, CA (US)

(72) Inventors: Alexander Lazarev, Lake Forest, CA (US); Pavel Lazarev, Menlo Park, CA (US); Delvin Tai Wai Yuk, Atherton, CA (US)

(73) Assignee: EosDx Inc., Mountain View, CA (US)

( * ) Notice: Subject to any disclaimer, the term of this patent is extended or adjusted under 35 U.S.C. 154(b) by 108 days.

This patent is subject to a terminal disclaimer.

(21) Appl. No.: 17/448,888

(22) Filed: Sep. 26, 2021

(65) Prior Publication Data

US 2022/0008027 A1 Jan. 13, 2022

Related U.S. Application Data

(63) Continuation of application No. 17/593,846, filed as application No. PCT/US2021/037224 on Jun. 14, 2021, now Pat. No. 11,607,188.

(Continued)

(51) Int. Cl.
*A61B 6/00* (2006.01)
*G16H 50/20* (2018.01)
(Continued)

(52) U.S. Cl.
CPC .............. *A61B 6/502* (2013.01); *A61B 6/467* (2013.01); *A61B 6/563* (2013.01); *G06T 7/0012* (2013.01);
(Continued)

(58) Field of Classification Search
CPC ......... A61B 6/467; A61B 6/481; A61B 6/502; A61B 6/504; A61B 6/5235; A61B 6/563;
(Continued)

(56) References Cited

U.S. PATENT DOCUMENTS

| 5,717,733 A | 2/1998 | Kurbatov et al. |
| 2015/0269323 A1 | 9/2015 | Ginsburg |

(Continued)

FOREIGN PATENT DOCUMENTS

| KR | 20180076702 A | 7/2018 |
| WO | 2021257451 A1 | 12/2021 |
| WO | 2021257457 A1 | 12/2021 |

OTHER PUBLICATIONS

James, "A Review of Low Angle Fibre Diffraction in the Diagnosis of Disease", British Journal of Medicine & Medical Research, 3(2): 383-397, Feb. 19, 2013.

(Continued)

*Primary Examiner* — Jon Eric C Morales
(74) *Attorney, Agent, or Firm* — MLO, a professional corp.

(57) ABSTRACT

An in vivo human-tissue analysis and communication system produces a quantitative diagnostic indicator for human-tissue analyzed by the system. The system includes a human-tissue-analyzer subsystem with at least one human-tissue analyzer constructed to analyze human tissue and to produce a quantitative-diagnostic indicator. There is also a two-way communication subsystem constructed to allow the human-tissue-analyzer subsystem to send and receive information relevant to the quantitative-diagnostic indicator. The human-tissue-analyzer subsystem includes at least one tissue diffractometer operatively coupled to a computer database over a network, and configured for acquisition of human-tissue data and transfer to the computer database over the network. A computer processor is operatively coupled to the tissue diffractometer, and the computer processor is configured to receive the human-tissue data from the tissue diffractometer, transmit the human-tissue data to the computer database; and process the human-tissue data (Continued)

using a data analytics algorithm that provides a quantitative-diagnostic indicator of human tissue.

33 Claims, 12 Drawing Sheets

Related U.S. Application Data

(60) Provisional application No. 63/039,345, filed on Jun. 15, 2020.

(51) Int. Cl.
*G16H 40/63* (2018.01)
*G16H 20/40* (2018.01)
*G16H 30/20* (2018.01)
*G16H 40/67* (2018.01)
*G06T 7/00* (2017.01)

(52) U.S. Cl.
CPC ............. *G16H 20/40* (2018.01); *G16H 30/20* (2018.01); *G16H 40/63* (2018.01); *G16H 40/67* (2018.01); *G16H 50/20* (2018.01); *G06T 2207/10116* (2013.01); *G06T 2207/30068* (2013.01)

(58) Field of Classification Search
CPC ........ G16H 15/00; G16H 20/40; G16H 30/20; G16H 40/63; G16H 40/67; G16H 50/20; G16H 50/70
See application file for complete search history.

(56) References Cited

U.S. PATENT DOCUMENTS

| | | |
|---|---|---|
| 2018/0038845 A1 | 2/2018 | Zimmermann et al. |
| 2018/0122499 A1 | 5/2018 | Austin et al. |
| 2019/0113451 A1 | 4/2019 | Weissleder et al. |
| 2020/0098476 A1 | 3/2020 | Loscutoff et al. |
| 2022/0013227 A1 | 1/2022 | Lazarev et al. |
| 2022/0013233 A1 | 1/2022 | Lazarev et al. |
| 2022/0415505 A1* | 12/2022 | Lazarev ................. G16H 15/00 |

OTHER PUBLICATIONS

James, "Fiber diffraction of skin and nails provides an accurate diagnosis of malignancies", Int. J. Cancer: 125, 133-138, 13 pages, Jul. 2009.

Ortiz et al, "Biomarkers of disease in human nails: a comprehensive review", Critical Reviews in Clinical Laboratory Sciences, Oct. 7, 2021, 18 pgs, Taylor & Francis Group.

Park, Hye Lyun, Authorized Officer, Korean Intellectual Property Office, "International Search Report" in connection with related International Application No. PCT/US2021/037238, dated Oct. 5, 2021, 5 pgs.

Park, Hye Lyun, Authorized Officer, Korean Intellectual Property Office, "Written Opinion of the International Searching Authority" in connection with related International Application No. PCT/US2021/037238, dated Oct. 5, 2021, 5 pgs.

Rodriguez, Kari, Authorized Officer, Commissioner for Patents, "International Search Report" in connection with related International Application No. PCT/US2021/037224, dated Sep. 29, 2021, 3 pgs.

Rodriguez, Kari, Authorized Officer, Commissioner for Patents, "Written Opinion of the International Searching Authority" in connection with related International Application No. PCT/US2021/037224, dated Sep. 29, 2021, 6 pgs.

Arboleda et al, Assessing lesion malignancy by scanning small-angle X-ray scattering of breast tissue with microcalcifications, Phys Med Biol. Aug. 7, 2019;64(15):155010, pp. 1-9.

Chapman et al., Diffraction enhanced x-ray imaging, Phys. Med. Biol. 42, Nov. 1997, pp. 2015-2025.

Conceicao et al, Analysis of breast cancer by small angle X-ray scattering (SAXS), Analyst, Apr. 2009 134(6):1077-82.

Moss et al., Correlation of X-ray diffraction signatures of breast tissue and their histopathological classification, Scientific Reports, Oct. 2017, pp. 1-9.

Oliver et al., Diffraction enhanced imaging utilizing a laser produced x-ray source, Rev. Sci. Instrum. 93, 093502, Sep. 2022, 7 pages.

Round et al., A preliminary study of breast cancer diagnosis using laboratory based small angle x-ray scattering, Phys Med Biol. Sep. 2005, 50(17):4159-68.

Sidhu et al., Mapping structural changes in breast tissue disease using x-ray scattering, Medical Physics 36, May 2009, pp. 3211-3217.

Yoneyama et al., Fast diffraction-enhanced imaging using continuous sample rotation and analyzer crystal scanning, J Synchrotron Radiat, Mar. 2020, pp. 468-471.

* cited by examiner

Figure 1.3: The levels of arrangement in fibrillar collagen in breast tissue. Typical dimensions taken from Fernandez et al. [51] (Printed with permission from Dr. M. Fernandez, 2009)

FIG. 3A             FIG. 3B
 
301        302
(a)        (b)
Figure 1.5: Electron micrographs of collagen tissue in (a) normal tissue and (b) invasive carcinoma tissue. In the normal tissue, the in-tact collagen fibres are aligned and well structured, where the collagen strands in the invasive carcinoma are broken and unstructured. (Printed with permission from Oxford University Press 2009, [96])

a SAXS pattern from a normal breast tissue biopsy a SAXS pattern from breast tissue with a known disease a SAXS pattern from breast tissue with a known disease

DIFFRACTOMETER-BASED GLOBAL IN SITU DIAGNOSTIC SYSTEM

CROSS-REFERENCE TO RELATED APPLICATIONS

This application is a continuation of U.S. patent application Ser. No. 17/593,846, filed Sep. 26, 2021 and entitled "Diffractometer-Based Global In Situ Diagnostic System", which application is a U.S. national phase application of International Application No. PCT/US2021/037224, filed Jun. 14, 2021, which in turn claims priority to U.S. Provisional Patent Application Ser. No. 63/039,345, filed Jun. 15, 2020, the disclosures which are incorporated herein by reference.

BACKGROUND

Early detection of cancer, e.g., breast cancer, may be correlated with increased survival rates. Absorptive imaging-based mammography techniques are widely used as diagnostic tools for detecting the presence of breast cancer but can suffer from poor contrast and other factors that can increase the difficulty of diagnosis based on the mammograms.

SUMMARY

An in vivo human-tissue analysis and communication system produces a quantitative diagnostic indicator for human-tissue analyzed by the system. The system includes a human-tissue-analyzer subsystem with at least one human-tissue analyzer constructed to analyze human tissue and to produce a quantitative-diagnostic indicator. There is also a two-way communication subsystem constructed to allow the human-tissue-analyzer subsystem to send and receive information relevant to the quantitative-diagnostic indicator. The human-tissue-analyzer subsystem includes at least one tissue diffractometer operatively coupled to a computer database over a network, and configured for acquisition of human-tissue data and transfer to the computer database over the network. A computer processor is operatively coupled to the tissue diffractometer, and the computer processor is configured to receive the human-tissue data from the tissue diffractometer, transmit the human-tissue data to the computer database; and process the human-tissue data using a data analytics algorithm that provides a quantitative-diagnostic indicator of human tissue.

Additional aspects and advantages of the disclosed concepts will become readily apparent to those skilled in the art upon review of the following detailed description, wherein only illustrative embodiments of the disclosed concepts are shown and described. As will be realized, the concepts of the present disclosure may be implemented in other and different embodiments, and the several details thereof are amenable to modification in various obvious respects, all without departing from the scope of the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIGS. 3A-3B show examples of collagen in normal tissue (FIG. 3A) and in invasive carcinoma tissue (FIG. 3B) (from: "Small Angle X-Ray Scattering as a Diagnostic Tool for Breast Cancer", Sabeena Sidhu, BSc, MSc School of Physics, Monash University, Feb. 12, 2009).

FIG. 5A: a SAXS pattern from a normal breast tissue biopsy. FIG. 5B: a SAXS pattern from a biopsy of diseased breast tissue.

FIG. 6A: a SAXS pattern from a biopsy of diseased breast tissue. FIG. 6B: a plot of scattering intensity as a function of q value.

DETAILED DESCRIPTION

Figure 1:
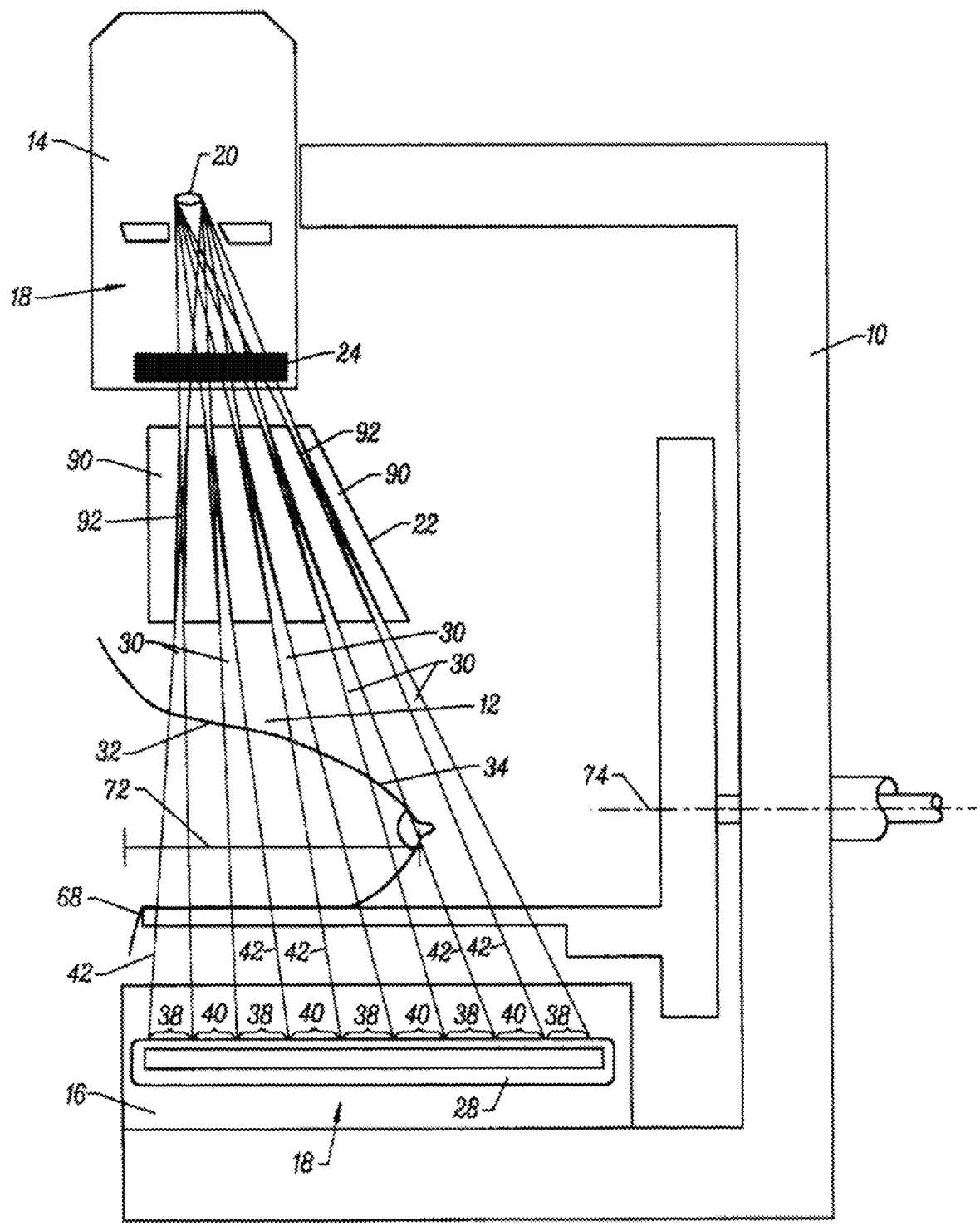
FIG. 1 shows an example of a multi beam x-ray diffraction system (from Komardin, et al., U.S. Pat. No. 6,175,117 B1).

Various embodiments of the invention have been shown and described herein for example purposes only. Numerous variations, changes, and substitutions are possible without departing from the invention. It should be understood that various alternatives to the embodiments of the invention described herein may be employed.

Systems and methods for providing a quantitative diagnostic indicator for a subject are disclosed. The systems may comprise a plurality of tissue diffractometers operably coupled to a computer database over a network, where the tissue diffractometers are configured to acquire small-angle x-ray scattering and/or wide-angle x-ray scattering data for a tissue within the subject. Optionally, the tissue diffractometers may also be configured to acquire absorptive images, e.g., mammography images, of the tissue. The system is configured to collect and process diffraction data, image data, and/or other data pertinent to the subject using a data analytics algorithm to provide a quantitative diagnostic indicator for the subject. The data analytics algorithm is randomly, periodically, or continually updated and refined using the data for a plurality of subjects stored in the computer database. In some instances, the quantitative diagnostic indicator may comprise an indicator of the likelihood that the subject has cancer or some other disease. In some instances, the quantitative diagnostic indicator may comprise a diagnosis that the subject has cancer or some other disease.

Whenever the phrase "at least," "greater than," or "greater than or equal to" precedes the first numerical value in a series of two or more numerical values, the phrase "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the phrase "no more than," "less than," or "less than or equal to" precedes the first numerical value in a series of two or more numerical values, the phrase "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

Unless otherwise defined, all of the terms and phrases used herein have the same meaning as commonly understood by a PHOSITA, a person having ordinary skill in the art that applies to this disclosure.

As used in this specification and the appended claims, the singular forms "a", "an", and "the" include plural references unless the context clearly dictates otherwise. Any reference to "or" herein is intended to encompass "and/or" unless otherwise stated.

As used herein, the phrase "tissue diffractometer" generally refers to a diffractometer configured to record diffraction data from one or more tissues. The tissue diffractometer may be an x-ray diffractometer. In some instances, the tissue diffractometer may be configured to record diffraction data and image data, e.g., mammograms.

As used herein, the phrase "quantitative-diagnostic indicator" refers to an indicator comprising quantitative-diagnostic information that may be generated with the help of one or more computer processors. The term "quantitative" has the meaning commonly understood by a PHOSITA. To clarify one aspect of that meaning, "quantitative" as used herein means that the corresponding diagnostic indicator is information that can be understood by anyone, without the need for professional interpretation by a health professional such as a medical doctor. In some instances, the "quantitative diagnostic indicator" may comprise a probability score for the likelihood that a subject has cancer, e.g., breast cancer. In some instances, the "quantitative diagnostic indicator" may comprise a diagnosis that a subject has cancer, e.g., breast cancer.

As used herein, the term "subject" generally refers to an animal, such as a mammal. A subject may be a human or non-human mammal. A subject may be afflicted with a disease or suspected of being afflicted with or having a disease. The subject may not be suspected of being afflicted with or having the disease. The subject may be symptomatic. Alternatively, the subject may be asymptomatic. In some cases, the subject may be treated to alleviate the symptoms of the disease or cure the subject of the disease. A subject may be a patient undergoing treatment by a healthcare provider.

As used herein, the phrase "healthcare provider" generally refers to a medical practitioner or support staff. The healthcare provider may be a doctor, a nurse, a dentist, a technician, a student, or the like. The healthcare provider may be at least partially responsible for the healthcare of the subject.

As used herein, the phrase "institution" generally refers to an entity related to one or more healthcare providers. The institution may be a medical center, a doctor's office, a clinic, a hospital, a university, or the like.

As used herein, the term "cancer" generally refers to a proliferative disorder caused or characterized by a proliferation of cells which have lost susceptibility to normal growth control. Cancers of the same tissue type usually originate in the same tissue and may be divided into different subtypes based on their biological characteristics. Non-limiting examples of categories of cancer are carcinoma (epithelial cell derived), sarcoma (connective tissue or mesodermal derived), leukemia (blood-forming tissue derived) and lymphoma (lymph tissue derived). Cancer may involve every organ and tissue of the body. Specific examples of cancers that do not limit the definition of cancer may include melanoma, leukemia, astrocytoma, glioblastoma, retinoblastoma, lymphoma, glioma, Hodgkin's lymphoma, and chronic lymphocytic leukemia. Examples of organs and tissues that may be affected by various cancers include pancreas, breast, thyroid, ovary, uterus, testis, prostate, pituitary gland, adrenal gland, kidney, stomach, esophagus, rectum, small intestine, colon, liver, gall bladder, head and neck, tongue, mouth, eye and orbit, bone, joints, brain, nervous system, skin, blood, nasopharyngeal tissue, lung, larynx, urinary tract, cervix, vagina, exocrine glands, and endocrine glands. In some cases, a cancer can be multicentric. In some cases, a cancer can be a cancer of unknown primary (CUP).

As used herein, the term "cloud" generally refers to shared or sharable storage of electronic data, e.g., a distributed network of computer servers. In some instances, the cloud may be used for archiving electronic data, sharing electronic data, and analyzing electronic data.

The methods and systems described herein are applied to characterization of tissues, e.g., soft tissues, within a subject, e.g., characterization of tissues in situ or in vivo. Examples of organs and tissues that may be characterized using the disclosed methods and systems include, but are not limited to, pancreas, breast, thyroid, ovary, uterus, testis, prostate, pituitary gland, adrenal gland, kidney, stomach, esophagus, rectum, small intestine, colon, liver, gall bladder, head and neck, tongue, mouth, eye and orbit, bone, joints, brain, nervous system, skin, blood, nasopharyngeal tissue, lung, larynx, urinary tract, cervix, vagina, exocrine glands, and endocrine glands.

Diffractometer-based systems and methods of use: In one aspect, the present disclosure provides a system that outputs a quantitative diagnostic indicator for a subject that may have or may be at risk for developing a disease, such as a proliferative disease or cancer. The system may comprise one or more tissue diffractometers operatively coupled to a computer database over a network. A tissue diffractometer of the one or more tissue diffractometers may be configured for transfer of image data, diffraction pattern data, subject data, or any combination thereof to the computer database over the network. The system may comprise one or more computer processors operatively coupled to the one or more diffractometers. The one or more computer processors may be individually or collectively configured to (i) receive the image data, diffraction pattern data, subject data, or any combination thereof from the one or more tissue diffractometers; (ii) transmit the image data, diffraction pattern data, subject data, or any combination thereof to the computer database; and (iii) process the image data, diffraction pattern data, subject data, or any combination thereof for a human subject using a data analytics algorithm that provides a quantitative diagnostic indicator for the human subject.

In another aspect, the present disclosure provides a method for generating a quantitative diagnostic indicator for a subject that may have or may be at risk for developing a disease, such as a proliferative disease or cancer. The method may comprise acquiring data comprising image data, diffraction pattern data, subject data, or any combination thereof for a human subject using one of a plurality of tissue diffractometers operatively coupled to a computer database over a network. The plurality of tissue diffractometers may be configured for transfer of the data to the computer database over the network. One or more computer processors may be operatively coupled to the plurality of tissue diffractometers. The one or more computer processors may be used to receive the data comprising image data, diffraction pattern data, subject data, or any combination thereof from the plurality of tissue diffractometers that are operatively coupled to a computer database over the network and may be configured for transfer of the data comprising the image data, diffraction pattern data, subject data, or any combination thereof to the computer database over the network. The data comprising the image data, diffraction pattern data, subject data, or any combination thereof may be transmitted to the computer database. The data comprising the image data, diffraction pattern data, subject data, or any combination thereof may be processed for the human subject using a data analytics algorithm that may provide a quantitative diagnostic indicator for the human subject. The following description may relate to both the method and the system.

In some instances, the one or more tissue diffractometers may be tissue diffractometers as described elsewhere herein. The one or more tissue diffractometers may be stand-alone tissue diffractometers (e.g., instruments or components of a system that do not comprise other functionalities). The one or more tissue diffractometers may be coupled with other instruments (e.g., the tissue diffractometer can be attached to or integrated with an absorption-based mammography imaging instrument). The operative coupling to a computer database may be over a local network (e.g., a local area network (LAN)) or a remote network (e.g., the internet).

In some instances, the image data may be images, image metadata, or the like, or any combination thereof. The images may be raw images (e.g., images as captured from a detector), processed images (e.g., images that have had one or more processing operations performed), image analogues (e.g., matrices of intensity values corresponding to pixels, vector representations of images), or the like. The image metadata may comprise non-image information regarding the conditions at which the image was acquired (e.g., x-ray wavelength, detector distance from the source and/or the sample, exposure time, date and time of acquisition, ambient conditions, etc.)

In some instances, the diffraction pattern data may comprise diffraction patterns, diffraction pattern metadata, or the like, or any combination thereof. The diffraction patterns may comprise diffraction patterns generated from an interaction of a radiation beam (e.g., an x-ray beam, a neutron beam) with a tissue. The diffraction patterns may comprise raw diffraction patterns, processed diffraction patterns, diffraction pattern analogues, or the like. The diffraction pattern metadata may comprise metadata as described elsewhere herein.

In some instances, the image data and/or diffraction pattern data may comprise data taken from both a healthy tissue and a tissue suspected of having an abnormality. Both the healthy tissue and the tissue suspected of having an abnormality may be of a same subject. For example, diffraction data can be taken from both a subject's breast suspected of having a cancer as well as the subject's other breast that is suspected of being free from the cancer.

In some instances, the human, also referred to herein in as subject, data may comprise an individual subject's age, sex, ancestry data, genetic data, behavioral data, medical history, previous medical tests or diagnostics, occupational data, social determinants of health, or any combination thereof. The ancestry data may be determined by one or more genetic tests. The ancestry data may comprise ancestry data reported by the subject. The genetic data may comprise genetic abnormalities, predispositions, or the like. For example, the subject data may comprise information regarding a subject's genetic predisposition to breast cancer (e.g., the presence or absence of a breast cancer gene).

In some instances, the computer database may be a cloud-based database, e.g., a database that resides on one or more remote computer servers. In some instances, the computer database may be a local computer database (e.g., a computer connected to a tissue diffractometer).

In some instances, the one or more computer processors may be computer processors that are part of one or more computer servers that host the computer database. In some instances, the one or more computer processors may be computers operatively coupled to the one or more tissue diffractometers (e.g., computers controlling the one or more diffractometers). The receiving of image data may comprise real-time or substantially real-time receipt of the image data. For example, in some instances, a stream of image data can be transmitted from a tissue diffractometer to the one or more computer processors as the images are being taken. In some instances, the image data may be transmitted in packets (e.g., bundles of one or more images). For example, a series of images of a plurality of subjects can be taken throughout a day and can then be all transmitted together. In another example, all images taken of a single subject during a single scan or single session can be transmitted together. The transmitting to the computer database may be real-time transmitting, substantially real-time transmitting, intermittent transmitting (e.g., transmitting packets), or any combination thereof.

In some instances, diffraction data processing and/or image data processing may occur between the receiving of the diffraction and/or image data and the transmitting of image data. For example, in some instances, the one or more computer processors may be configured to compress the diffraction and/or image data to improve the transfer speed to the database. In another example, the one or more computer processors can be configured to extract relevant parameters (e.g., d spacings, pair distribution functions) from the data (e.g., diffraction pattern data) before transmitting to the computer database, thereby significantly decreasing the amount of data to be transmitted. In some instances, the processing of diffraction and/or image data may be performed after the data has been transferred to the computer database. The processing of the diffraction and/or image data may be local processing (e.g., processing on a computer local to the tissue diffractometers) or remote processing (e.g., processing on a remote computer server or cloud-based server). In some instances, the data processing may comprise the application of a statistical analysis and/or machine learning algorithm (which individually or collectively may be referred to as a "data analytics algorithm" herein). The data processing may comprise processing diffraction data and/or image data for a single subject or a plurality of subjects. For example, the diffraction and/or image data acquired for a single subject can be processed to generate the quantitative diagnostic indicator for the subject. In another example, diffraction data and/or image data from a plurality of subjects may be processed to refine the data analytics algorithm and/or to generate a baseline diagnostic indicator.

In some instances, the system may further comprise a user interface. The user interface may be configured to allow an individual subject and/or their healthcare provider to upload the individual subject's image data, diffraction pattern data, subject data, or any combination thereof to the computer database. The uploading the individual subject's image data, diffraction pattern data, subject data, or any combination thereof to the computer database may be in exchange for processing the individual subject's image data, diffraction patter data, or any combination thereof to receive the quantitative diagnostic indicator for the individual subject. For example, a healthcare provider can use the user interface to upload diffraction images of a suspicious mass identified in a mammogram, along with the absorption-based mammography images, to the computer database. In this example, the system comprising the one or more computer processors and the computer database can then process the diffraction images, as well as the absorption-based mammography images, using a data analytics algorithm to generate a diagnostic indicator that is provided to the healthcare provider. In some instances, the diffraction images and the absorption-based mammography images may be retained on the computer database, where they can be used to refine the data analytics algorithm that generates the diagnostic indicator. The user interface may be configured to allow an individual subject and/or their healthcare provider to make payments and/or upload the individual subject's signed consent form. The payments may be cash payments (e.g., the user interface displays an address to send the payments), check payments (e.g., paper or electronic check payments), card payments (e.g., credit or debit card payment processing), app-based payments (e.g., PayPal®, Venmo®), cryptocurrency payments (e.g., Bitcoin), or any combination thereof. For example, in some instances, an individual subject may pay via a health savings account debit card. The signed consent form may be signed by the individual subject and/or the healthcare provider. The signed consent form may be related to the quantitative diagnostic indicator. For example, the individual subject can sign and upload a consent form stating that the subject's diffraction and/or image data may be retained on the computer database. In some instances, the signed consent form may be physically signed, electronically signed, or any combination thereof.

In some instances, a system of the present disclosure may comprise 1, 2, 3, 4, 5, 6, 7, 8, 9, 10, 20, 30, 40, 50, 60, 70, 80, 90, 100, 150, 200, 250, 300, 350, 400, 450, 500, or more than 500 tissue diffractometers. In some instances, the number of tissue diffractometers in the system may range between any two of the values specified in this paragraph. For example, in some instances, the number of tissue diffractometers in the system may range from 4 to 100. Those of skill in the art will recognize that in some instances, the number of tissue diffractometers in the system may have any value within the range of values specified in this paragraph, e.g., 125 tissue diffractometers.

The one or more tissue diffractometers may be two or more tissue diffractometers located in two or more different geographic locations. For example, a first tissue diffractometer in a first location can send one set of image data to the one or more computer processors while a second tissue diffractometer in a second location can send one set of diffraction pattern data to the one or more computer processors. In this example, the image data and the diffraction pattern data can both be used to refine the data analytics algorithm that generates quantitative diagnostic indicators for individual subjects, and may also both be retained on the computer database. The one or more tissue diffractometers may comprise a data encryption device. The data encryption device may comprise a global positioning system (GPS) positioning sensor. The data encryption device may generate encrypted image data, diffraction pattern data, subject data, or any combination thereof. The encrypted image data, diffraction pattern data, subject data, or any combination thereof may be transferred to the computer database. The encrypted image data, diffraction pattern data, subject data, or any combination thereof may comprise data regarding changes in a location of the one or more tissue diffractometers. For example, the image metadata generated by a tissue diffractometer can comprise location information for that tissue diffractometer. In this example, a movement of the tissue diffractometer can be tracked using the image metadata transmitted by the tissue diffractometer. In another example, the GPS positioning sensor can be in constant communication with the computer database regarding the location of the tissue diffractometer. The inclusion of the GPS sensor may reduce a likelihood that the tissue diffractometer is stolen or misappropriated by untrained users. The data encryption device may be configured to encrypt the data in line with a health data privacy standard. For example, the encryption device may make the transmission and storage of the image data, diffraction pattern data, subject data, or any combination thereof compliant with the Health Insurance Portability and Accountability Act (HIPAA). The data encryption device may comprise a module configured to only permit communication between the tissue diffractometer and the computer database. For example, other network communications can be disabled such that the data from the tissue diffractometer can be sent only to the computer database.

In some instances, the plurality of tissue diffractometers that are operatively coupled to the system may be located in 2, 3, 4, 5, 6, 7, 8, 9, 10, 20, 30, 40, 50, 60, 70, 80, 90, 100, 150, 200, 250, 300, 350, 400, 450, 500, or more than 500 different geographical locations (thereby effectively constituting a global diagnostics system). In some instances, the number of different geographical locations comprising tissue diffractometers that are operatively coupled to the system may range between any two of the values specified in this paragraph. For example, in some instances, the number of different geographical locations included in the system may range from 8 to 20. Those of skill in the art will recognize that in some instances, the number of different geographical locations included in the system may have any value within the range of values specified in this paragraph, e.g., 14 different geographical locations.

Small angle x-ray scattering: In some instances, the one or more tissue diffractometers may be configured to perform small angle x-ray scattering (SAXS) measurements. The SAXS measurements may comprise measurements of the long-range ordering of the tissue. For example, the SAXS measurement can record measurements of tissue order in the range of 10 to 1,000 nanometers. The SAXS measurements may comprise measurements of scattering of at least about 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.6, 7, 7.5, 8, 8.5, 9, 9.5, 10, or more degrees. The SAXS measurements may comprise measurements of at most about 10, 9.5, 9, 8.5, 8, 7.5, 7, 6.5, 6, 5.5, 5, 4.5, 4, 3.5, 3, 2.5, 2, 1.5, 1, 0.9, 0.8, 0.7, 0.6, 0.5, 0.4, 0.3, 0.2, 0.1, 0.05, 0.01, or less degrees. The SAXS measurements may comprise measurements of a range as defined by any two of the preceding numbers. For example, the SAXS measurements may comprise measurements of scattering of 0.1-10 degrees. The SAXS measurements may comprise measurements with respect to degrees (e.g., $\theta$), $2\theta$, d (e.g., distance measured in Angstroms), q (e.g., 1/d), or the like, or any combination thereof.

Wide angle x-ray scattering: In some instances, the one or more tissue diffractometers may be configured to perform wide angle x-ray scattering (WAXS) measurements. The WAXS measurements may comprise measurements of the short-range ordering of the tissue. For example, the WAXS measurements can record measurements of the tissue order below 10 nanometers. The WAXS measurements may provide structural information about non-tissue objects in the tissue. For example, a WAXS measurement of an object suspected of being a breast calcification can confirm that the object is composed of calcium oxalate and calcium phosphate. In another example, a WAXS measurement can generate information regarding a molecular structure within a tissue. The WAXS measurements may comprise measurements of at least about 10, 15, 20, 25, 30, 35, 40, 45, or more degrees. The WAXS measurements may comprise measurements of at most about 45, 40, 35, 30, 25, 20, 15, 10, or less degrees. The WAXS measurements may comprise measurements of a range as defined by any two of the preceding numbers. For example, the WAXS measurements can comprise measurements of scattering of 10-45 degrees. The WAXS measurements may comprise measurements with respect to degrees (e.g., $\theta$), $2\theta$, d (e.g., distance measured in Angstroms), q (e.g., 1/d), or the like, or any combination thereof.

Mammography: in some instances, the one or more tissue diffractometers may be configured to perform mammography. The mammography may be absorptive, imaging-based mammography. For example, a beam of x-rays can be projected through a breast and the absorption profile of the breast can be recorded. The one or more tissue diffractometers may be coupled to, or integrated with, an existing mammography instrument to add tissue diffractometry capabilities to the mammography instrument. Thus, in some instances, the tissue diffractometers of the present disclosure may be configured to perform SAXS, WAXS, mammography, or any combination thereof. In some instances, the mammography may be performed using an energy source other than the energy source used to measure diffraction patterns. For example, the mammography may be performed using a 19 keV x-ray source and the diffraction pattern may be generated using a 75 keV source. In another example, the mammography can be performed with a source optimized for image quality and contrast, while the diffraction source can be a molybdenum or silver source. The one or more tissue diffractometers may be configured to perform mammography via scanning. For example, an x-ray beam can be rastered through the breast tissue of a subject and the absorption of the breast tissue can be recorded. A set of target coordinates for directing an x-ray beam may be determined from a mammogram. For example, a mammogram can be performed and, based on the mammogram, areas of ambiguity (e.g., areas suspected of comprising a cancer or other diseased tissue) can be identified. In this example, the location(s) of the suspect area(s) as determined from the mammogram can be used to determine target coordinates and direct a tissue diffractometer to measure a diffraction pattern within one of the areas to provide additional information about the state of the area. The tissue diffractometer may collect diffraction pattern data from the area located by the target coordinates while the subject is still in the mammography instrument. For example, the target coordinates can be generated using absorptive imaging mammography, the absorptive imaging mammography x-ray source and detector can be moved, the tissue diffractometer can be moved into position, and the tissue diffractometer can measure diffraction patterns. In this example, the subject can remain in position within the hybrid tissue diffractometer/mammography instrument to decrease the complexity of mapping the target coordinates of the suspect area(s).

Computer database: As noted above, in some instances, the computer database may reside on a central computer server. In some instances, the central computer server may reside in the cloud (e.g., may be a cloud-based computer server comprising a distributed network of remote computer servers). In some instances, the computer database may reside on a local server. In some instances, data may be transferred or exchanged between a local computer database and a remote or central computer database. The computer database may reside on a privacy law compliant server (e.g., a HIPAA compliant server).

In some instances, the image data, diffraction pattern data, subject data, or any combination thereof transferred to the computer database may be depersonalized before transfer. The depersonalization may comprise removal of personally identifiable information (e.g., name, patient number, social security number, address, etc.). For example, identifying information can be removed from image metadata and/or subject data before the image metadata and/or subject data are transferred to the computer database. The depersonalization of the image data, diffraction pattern data, subject data, or any combination thereof may aid in making the computer database compliant with privacy laws. In some instances, a key for mapping depersonalized image data, diffraction pattern data, subject data, or any combination thereof stored in the computer database to an individual subject may be stored in a local institutional database and/or in the individual subject's personal files. For example, a key can be generated that relates a subject to their depersonalized data for later reference or reunification. The local institutional database may be a database operated by the institution where the subject went to obtain the image data, diffraction pattern data, subject data, or any combination thereof. For example, a hospital can have a database comprising keys to link the identities of hospital patients to their depersonalized data. In another example, the key can be kept in the patient's personal medical files.

Data analytics algorithm: As noted above, in some instances the data analytics algorithm may comprise a statistical analysis of diffraction pattern data and/or a function thereof. In some instances, the data analytics algorithms may comprise a statistical analysis of image data, diffraction pattern data, subject data, a function of any of the preceding, or any combination thereof. In some instances, the statistical analysis may comprise determination of a pair-wise distance distribution function, determination of a Patterson function, a calculation of a Porod invariant, Fourier transformation and calculation of pair-wise distance distribution function, a cluster analysis, a dispersion analysis, determination of one or more molecular structural periodicities, or any combination thereof. The statistical analysis may comprise a determination of a structural periodicity of a tissue or a tissue feature. The structural analysis may comprise a determination of a structural periodicity of collagen, one or more lipids, or a combination thereof. For example, a diffraction pattern can provide information regarding the structural periodicity, and thus the relative degree of ordering, of the collagen within the spot size of the diffractometer. In another example, the ordering of lipid layers can be determined by diffraction, which can give information about the stiffness of the lipid layers and the chemical composition of the layers (e.g., the amount of cholesterol or other stiffening agents) on a local level. In some instances, the structural periodicity of the tissue may be used to determine a likelihood of a cancer being present within the tissue. For example, FIG. 3A shows an electron microscope image of normal collagen tissue, while FIG. 3B shows an electron microscope image of collagen in an invasive carcinoma tissue. In this example, the collagen in the normal tissue is more well-structured, which can give rise to stronger diffraction peaks, while the collagen in the carcinoma is poorly structured, which can result in weak diffraction peaks.

In some instances, the data analytics algorithm may comprise or further comprise the use of one or more machine learning algorithms. The one or more machine learning algorithms may be configured to operate upon image data, diffraction pattern data, subject data, or any combination thereof. The machine learning algorithm may comprise one or more supervised learning algorithms, one or more unsupervised learning algorithms, one or more semi-supervised learning algorithms, one or more reinforcement learning algorithms, one or more deep learning algorithms, or any combination thereof. The machine learning algorithm may be a deep learning algorithm. The deep learning algorithm may comprise one or more convolutional neural networks, one or more recurrent neural networks, and/or one or more recurrent convolutional neural networks.

Statistical analysis algorithms and/or machine learning algorithms implemented on a local computer or a remote server may be used to perform data analytics. For example, a machine learning algorithm can be configured to pre-process raw image data, diffraction pattern data, and/or subject data to remove noise or other artifacts. A different machine learning can be trained to identify features within the image data, diffraction pattern data, and/or subject data. Such a machine learning algorithm can cluster data points for use as an identification algorithm. Other machine learning algorithms can be configured to provide a quantitative diagnostic indicator.

The machine learning algorithms may comprise a supervised, semi-supervised, or unsupervised machine learning algorithm. A supervised machine learning algorithm, for example, is an algorithm that is trained using labeled training data sets, e.g., data sets that comprise training inputs with known outputs. The training inputs can be provided to an untrained or partially trained version of the machine learning algorithm to generate a predicted output. The predicted output can be compared to the known output in an iterative process, and if there is a difference, the parameters of the machine learning algorithm can be updated. A semi-supervised machine learning algorithm is trained using a large set of unlabeled training data, e.g., unlabeled training inputs, and a small number of labeled training inputs. An unsupervised machine learning algorithm, e.g., a clustering algorithm, may find previously unknown patterns in data sets comprising data with no pre-existing labels.

One non-limiting example of a machine learning algorithm that can be used to perform some of the functions described above, e.g., processing of diffraction data, image data, and/or generating quantitative diagnostic indicators, is a neural network. Neural networks employ multiple layers of operations to predict one or more outputs, e.g., a likelihood that a subject has cancer, from one or more inputs, e.g., image data, diffraction pattern data, subject data, processed data derived from image data, diffraction pattern data, and/or subject data, or any combination thereof. Neural networks can include one or more hidden layers situated between an input layer and an output layer. The output of each layer can be used as input to another layer, e.g., the next hidden layer or the output layer. Each layer of a neural network can specify one or more transformation operations to be performed on the data input to the layer. Such transformation operations may be referred to as "neurons". The output of a particular neuron may be, for example, a weighted sum of the inputs to the neuron, that is optionally adjusted with a bias and/or multiplied by an activation function, e.g., a rectified linear unit (ReLU) or a sigmoid function.

Training a neural network can involve providing inputs to the untrained neural network to generate predicted outputs, comparing the predicted outputs to expected outputs, and updating the algorithm's weights and biases in an iterative manner to account for the difference between the predicted outputs and the expected outputs. For example, a cost function can be used to calculate a difference between the predicted outputs and the expected outputs. By computing the derivative of the cost function with respect to the weights and biases of the network, the weights and biases can be iteratively adjusted over multiple cycles to minimize the cost function. Training may be complete when the predicted outputs satisfy a convergence condition, such as obtaining a small magnitude of calculated cost.

Convolutional neural networks (CNNs) and recurrent neural networks can be used to classify or make predictions from image data, diffraction pattern data, subject data, or any combination thereof. CNNs are neural networks in which neurons in some layers, called convolutional layers, receive data from only small portions of a data set. These small portions may be referred to as the neurons' receptive fields. Each neuron in such a convolutional layer may have the same weights. In this way, the convolutional layer can detect features, e.g., cancerous growths, in any portion of the input image data, diffraction data, or a combination thereof.

RNNs, meanwhile, are neural networks with cyclical connections that can encode dependencies in time-series data, e.g., longitudinal study images of one or more subjects. An RNN may include an input layer that is configured to receive a sequence of time-series inputs, e.g., image data, diffraction pattern data, subject data, or any combination thereof collected over a period of time. An RNN may also include one or more hidden recurrent layers that maintain a state. At each time step, each hidden recurrent layer can compute an output and a next state for the layer. The next state can depend on the previous state and the current input. The state can be maintained across time steps and can capture dependencies in the input sequence. Such an RNN can be used to determine time-series features or evolutions of features within the subject data.

One example of an RNN is a long short-term memory network (LSTM), which can be made of LSTM units. An LSTM unit can be made of a cell, an input gate, an output gate, and a forget gate. The cell can be responsible for keeping track of the dependencies between the elements in the input sequence. The input gate can control the extent to which a new value flows into the cell, the forget gate can control the extent to which a value remains in the cell, and the output gate can control the extent to which the value in the cell is used to compute the output activation of the LSTM unit. The activation function of the LSTM gate may be, for example, the logistic function.

Other examples of machine learning algorithms that can be used to process image data, diffraction pattern data, subject data, or any combination thereof are regression algorithms, decision trees, support vector machines, Bayesian networks, clustering algorithms, reinforcement learning algorithms, and the like.

The clustering algorithm may be, for example, a hierarchical clustering algorithm. A hierarchical clustering algorithm can be a clustering algorithm that clusters objects based on their proximity to other objects. For example, a hierarchical clustering algorithm can cluster image data, diffraction pattern data, subject data, or any combination thereof. The clustering algorithm can alternatively be a centroid-based clustering algorithm, e.g., a k-means clustering algorithm. A k-means clustering algorithm can partition n observations into k clusters, where each observation belongs to the cluster with the nearest mean. The mean can serve as a prototype for the cluster. In the context of image data, diffraction pattern data, subject data, or any combination thereof, a k-means clustering algorithm can generate distinct groups of data that are correlated with each other. Thereafter, each group of data can be associated with, e.g., a particular probability or diagnosis of cancer, based on knowledge about that subsystem, e.g., knowledge about previous diagnoses and data. The clustering algorithm can alternatively be a distribution-based clustering algorithm, e.g., a Gaussian mixture model or expectation maximization algorithm. Examples of other clustering algorithms are cosine similarity algorithms, topological data analysis algorithms, and hierarchical density-based clustering of applications with noise (HDB-SCAN).

The machine learning algorithm may be trained using a training dataset comprising image data, diffraction pattern data, subject data, or any combination thereof. The training dataset may be stored in the computer database for a specific pathology and/or physiological norm group. The training dataset may be obtained using the one or more tissue diffractometers. The training dataset may comprise absorptive mammography images. The training dataset may comprise information regarding a confirmation of a diagnosis for given set of data. For example, data comprising a plurality of images and diffraction patterns of a tissue suspected of being cancerous can also comprise a histological confirmation of the presence of the cancer in the tissue. In another example, a set of diffraction images can be accompanied by data regarding the longevity of the subject that the diffraction images were taken from. The computer database for the specific pathology and/or physiological norm group may be a remote computer database (e.g., a cloud-based database) or a local database (e.g., a computer system local to a tissue diffractometer). For example, the training dataset for breast cancer diagnostic indicators can be stored on a computer database with other breast cancer diagnostic data. The training dataset may be updated as new image data, diffraction pattern data, subject data, or any combination thereof is uploaded to the computer database. The updating may be an inclusion of the new data, a removal of the old data, or a combination thereof. For example, new image data can be added to the training dataset as it is taken to improve the quality of the training dataset. In another example, poor quality data may be removed from the training dataset when higher quality new data is added. The statistical analysis algorithm and/or machine learning algorithm (e.g., the data analytics algorithm) may be updated when the computer database or training dataset residing thereon is updated. For example, a machine learning algorithm can be retrained using the new training dataset to improve the efficacy of the machine learning algorithm in generating a quantitative diagnostic indicator. The statistical analysis and/or machine learning algorithm may be continuously, periodically, or randomly updated and refined as the training dataset is updated. In this example, the revised statistical analysis and/or machine learning algorithm may be more accurate, specific, and/or sensitive in providing a probability or diagnosis than a previous version derived from a previous training dataset was.

Quantitative diagnostic indicator: In some instances, the quantitative diagnostic indicator for the individual subject may comprise an indicator of a likelihood that the individual subject has a cancer or other disease. The quantitative diagnostic indicator for the individual subject may comprise an indicator of a likelihood that the individual subject has breast cancer. For example, a quantitative diagnostic indicator can comprise a banded risk assessment for the individual subject (e.g., high risk, medium risk, low risk). The quantitative diagnostic indicator may be displayed on a user interface of a device (e.g., a user interface on a computer screen, a user interface on a tablet). The quantitative diagnostic indicator may be a report. The report may be a printed report. The report may comprise additional information. For example, the report may comprise a likelihood of the subject having a cancer, as well as the indicators that contributed to the generation of the report and a suggestion of possible next steps for the subject to take. The indicator may be a percentage (e.g., a percentage likelihood that the subject has the cancer), a risk band (e.g., high risk, medium risk, low risk), a comparison of factors (e.g., a list of factor indication a presence and a list of factors indicating an absence), or the like, or any combination thereof. The indicator of the likelihood that the individual subject has cancer may be an indicator of the likelihood that the individual subject has breast cancer.

In some instances, the quantitative diagnostic indicator for the individual subject may comprise a diagnosis that the individual subject has a cancer or other disease. The quantitative diagnostic indicator for the individual subject may comprise a diagnosis that the individual subject has breast cancer. The quantitative diagnostic indicator may be generated at least in part using a statistical analysis algorithm and/or a machine learning algorithm. The quantitative diagnostic indicator may be generated at least in part using input from a healthcare provider. For example, the healthcare provider can be presented with a list of indicators and risk bands, and the healthcare provider can make a final determination as to the diagnosis of the subject. In some instances, the quantitative diagnostic indicator may have an accuracy, selectivity, and/or specificity of at least about 10%, 20%, 30%, 40%, 50%, 60%, 70%, 80%, 90%, 95%, 98%, 99%, 99.9%, or more. In some instances, the quantitative diagnostic indicator may have an accuracy, selectivity, and/or specificity of at most about 99.9%, 99%, 98%, 95%, 90%, 80%, 70%, 60%, 50%, 40%, 30%, 20%, 10%, or less. Any of the lower and upper values described in this paragraph may be combined to form a range included within the present disclosure, for example, in some instances the quantitative diagnostic indicator may have an accuracy, selectivity, and/or specificity that ranges from about 80% to about 99%. Those of skill in the art will recognize that, in some instances, the quantitative diagnostic indicator may have an accuracy, selectivity, and/or specificity that has any value within this range, e.g., about 98.6%.

FIG. 1 shows an example of a multi beam x-ray diffraction system configured for acquiring diffraction data for a subject's (e.g., a patient's) breast. The diffraction system comprises a frame 10 that includes a breast positioning area 12, an upper optics housing 14 and a lower optics housing 16. The upper optics housing 14 and the lower optics housing 16 include an optics assembly 18. The optics assembly 18 includes a radiation source 20, a beam forming apparatus 22 and an adjustable diaphragm 24 positioned in the upper optics housing 14. The optics assembly 18 also includes a filter and a two-dimensional detector 28 positioned in the lower optics housing 16. The breast positioning area 12 can include a breast holder 68 such as a single plate on which the breast 32 is rested. Because the process of identifying the substances which make up an analysis section is not dependent on having a consistent thickness of the breast 32, the compression of the breast 32 which typically occurs in mammography apparatus can be eliminated. The plate should be transparent to the radiation and cause minimal scattering. In another instance the breast positioning area 12 includes a breast holder 68 consisting of an upper plate and a lower plate which can be moved toward one another to compress the breast 32 during the analysis. The plates are constructed from a material which allows the radiation to pass through the plates. Suitable materials for the plate include, but are not limited to, polyethylene, non-crystalline glass and silicon dioxide. In another instance, the breast positioning area does not include any structure for supporting the breast 32. During the analysis the patient need only hold still.

The frame 10 can be rotated about an axis 74 as indicated. The rotation does not affect the position of the breast 32 or any breast holder 68 within the breast positioning area 12. As a result, the rotation allows a scan and analysis from particular projections. The axis 74 of rotation is as close to the center of the breast 32 as is possible to preserve the distance between the detector 28 and the breast 32 at each projection.

In operation, the beam forming apparatus 22 forms the radiation into a weakly diverging incident beam 30. The incident beam 30 is sufficiently long to be incident on one entire dimension of a breast 32 positioned in the breast positioning area 12. In FIG. 1, the breast 32 is positioned so the incident beam 30 is incident on the entire width of the breast 32, i.e. the length of the incident beam 30 extends into and out of the plane of the page. The beam forming apparatus 22 is preferably positioned around 10 cm from the upper surface 34 of the breast 32. A suitable beam forming apparatus 22 includes, but is not limited to, a Kratki collimator.

The incident beam 30 passes from the beam forming apparatus 22 through the breast 32 to the detector 28. The detector 28 receives radiation in a transmitted beam zone 38 and a scattering zone 40. The transmitted beam zone 38 receives the transmitted beam 42 and the scattering zone 40 receives radiation scattered outside the transmitted beam 42 by the breast 32.

The beam forming apparatus 22 can include a plurality of transparent channels 90 and opaque channels 92 as illustrated in FIG. 1. The radiation from the radiation source 20 passes through the transparent channels 90 to form a plurality of weakly divergent incident beams 30. Each incident beam 30 has a length sufficient to cover the entire width of the breast 32. The beam forming apparatus 22 allows a plurality of analysis sections to be analyzed during a single exposure of the breast 32. Accordingly, the subject's exposure time can be reduced. The transparent channels 90 of the beam forming apparatus 22 are oriented along directions converging at a point coinciding with the focal point of the radiation source 20. Suitable beam forming apparatuses 22 include, but are not limited to, a slit raster. Further, suitable shapes and arrangements for the transparent channels 90 include, but are not limited to, slits and round apertures located at vertices of hexagonal or square lattices. The transparent channels 90 should converge at the focal spot of the source to increase energy yield of the device. The beam forming apparatus 22 can form incident beams 30 which are spaced along an entire dimension of the breast 32, however, the overlap of scattered radiation from adjacent transmitted beams 42 should be minimized. When the beam forming apparatus 22 is a slit raster, suitable widths for the transparent channels 90 include, but are not limited to 20-120 µm, 40-80 µm, and 55-65 µm. When the beam forming apparatus 22 is a slit raster, the width of the opaque sections depends on the desired number of incident beams which are incident on the breast. A suitable width of the opaque section includes, but is not limited to, 0.5 centimeter. When the beam forming apparatus 22 is a slit raster, suitable depths for the transparent channels are on the order of 100 mm depending on the desired divergence of the incident beam. Suitable beam divergences include, but are not limited, to 1-10 arc seconds. The plurality of incident beams 30 can reduce the scan time. For instance, when the incident beams 30 are evenly spaced across the length 72 of the breast 32, the upper optics housing 14 can move a distance roughly equal to the displacement between the incident beams 30 to scan the entire breast 32. This reduced scan time helps to increase the subject's comfort.

Figure 2A:
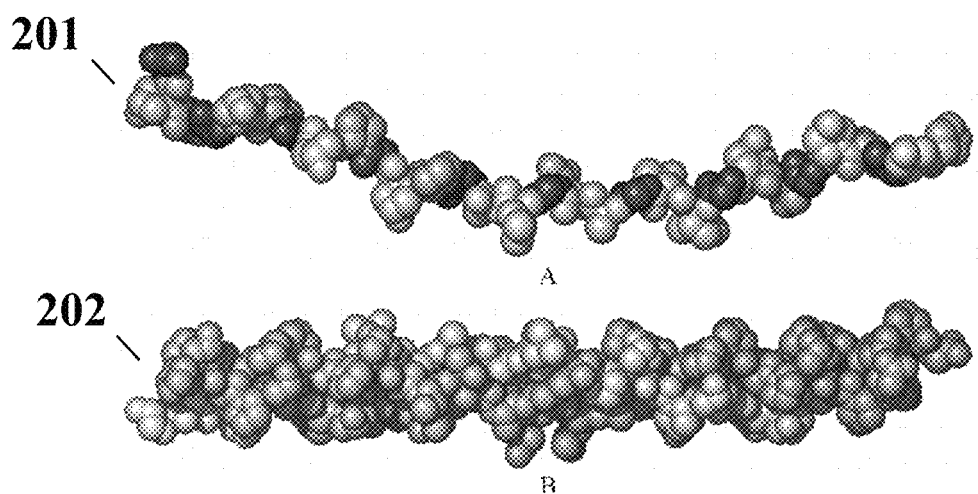
FIG. 2A shows an example of a disordered molecule and an ordered molecule.

FIG. 2A shows an example of a disordered molecule and an ordered molecule. The disordered molecule 201 may exhibit less efficient packing than the ordered molecule 202. As such, a diffraction pattern taken of a plurality of disordered molecules may have less prominent peaks due to the lack of ordered packing. For example, an x-ray diffraction image of solid sodium oleate can be broader than the corresponding x-ray diffraction image of sodium stearate due to the stearate having less disorder. The relationship between ordering and x-ray diffraction pattern intensity can be extended to larger biological systems (e.g., proteins, cell walls, fibers, muscles, etc.). For example, a well-ordered array of muscle fibers can have a stronger x-ray diffraction pattern than a disordered array. If a biological system shows a different ordering behavior when it is healthy versus anomalous, x-ray diffraction can provide information about the health of the tissue. For example, a mammograph can show small white deposits in a breast. In this example, an unhealthy breast tissue with solid calcium deposits can be discerned from dense healthy breast tissue using WAXS to determine the molecular identity of the white deposits. In another example, collagen tends to be well ordered in healthy tissues but disordered in unhealthy tissues. In this example, a SAXS measurement of the tissue can determine the disorder state of the collagen and thus determine if the tissue is abnormal. Examples of deposits discernable by WAXS may include urea deposits (e.g., in gout), calcium deposits (e.g., calcium deposits in breast tissue), other organic crystals (e.g., proteins), other inorganic crystals (e.g., calcium fluoride), organic-inorganic crystalline hybrids (e.g., hemoglobin buildup), or the like, or any combination thereof. Examples of conditions discernable by SAXS may include cancers (e.g., carcinoma), plaque buildups, muscular diseases (e.g., atrophy), subcutaneous warts, or the like.

Figure 2B:
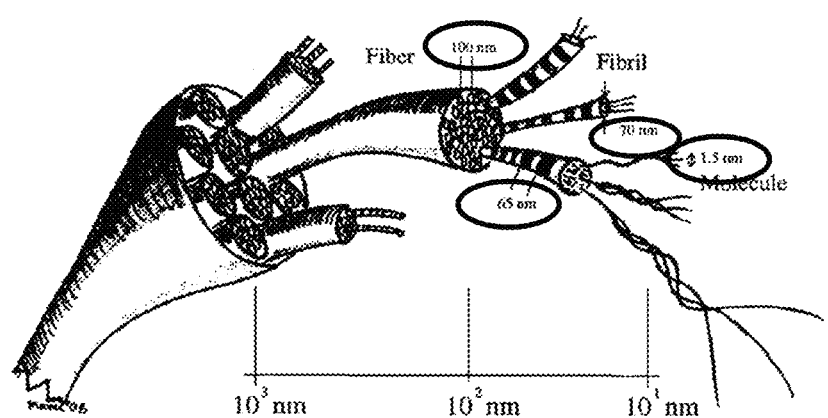
FIG. 2B shows an example of the relative scales of various biological objects (from "Small Angle X-Ray Scattering as a Diagnostic Tool for Breast Cancer", Sabeena Sidhu, BSc, MSc School of Physics, Monash University, Feb. 12, 2009).

FIG. 2B shows an example of the scales of various biological objects. The different scales may highlight the advantage of measuring SAXS, WAXS, absorptive mammography images, or any combination thereof at a same time. For example, an absorptive mammography image can have a resolution of approximately 0.1 millimeters per pixel, which can make it impossible to view features on the order of 100 micrometers or below. In this example, SAXS can provide details about the presence of ordering on the order of 10-10,000 nanometers and WAXS can provide details about the presence of ordering on the order of 0.1-10 nanometers. As shown in FIG. 2B, much of the fibrillar collagen in breast tissue may be of a scale of less than 100 micrometers, so information about the ordering of the collagen can be undetected by absorptive mammography but can be detected using x-ray scattering methods. Because tissue abnormalities can result in a change in the ordering of the tissue (e.g., cancer can disrupt collagen ordering), SAXS and/or WAXS can be a valuable addition to absorptive mammography.

FIGS. 3A-3B show examples of electron micrographs of collagen in normal tissue and in invasive carcinoma tissue. The healthy collagen 301 in FIG. 3A may present as a well-ordered tissue. The ordering of the fibrils, along with the homogenous nature of all of the tissue, can give rise to a strong diffraction pattern with peaks corresponding to the axial and meridional lengths of the collagen. The presence of these peaks can be an indicator of a healthy tissue. For example, a machine learning algorithm can be trained in part using healthy collagen tissues to associate the presence of diffraction peaks corresponding to the axial and meridional dimensions of the collagen with a healthy tissue. The invasive carcinoma tissue 302 of FIG. 3B may lack the long ranger ordering of the healthy tissue 301. As a result, a diffraction pattern taken of carcinoma tissue 302 may have weak or non-existent collagen peaks. This lack of peaks may be an indication of an invasive carcinoma. For example, a machine learning algorithm can use the lack of collagen peaks where there are expected to be collagen peaks as an indication of a presence of an invasive carcinoma.

Figure 4:
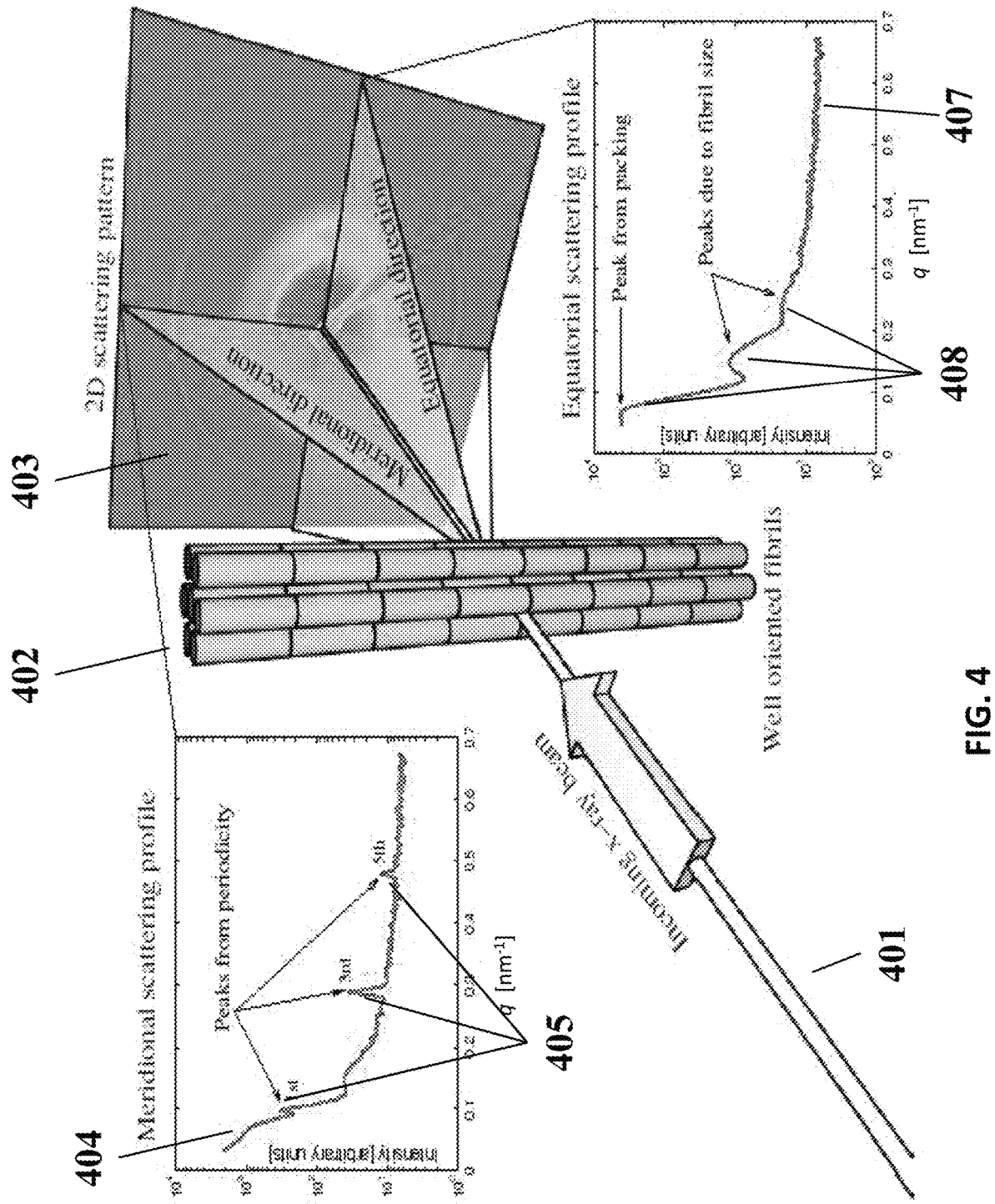
FIG. 4 shows examples of x-ray diffraction data generation.

FIG. 4 shows x-ray diffraction data generation. Incoming x-ray beam 401 can be directed towards fibril bundle 402. The periodicity of fibril bundle 402 can give rise to x-ray diffraction, which can be recorded as x-ray diffraction pattern 403. The intensity along the meridional axis of diffraction pattern 403 can be taken from the center of the pattern to the edge and can be plotted as meridional scattering profile 404. The meridional scattering profile can comprise peaks 405. The peaks can be the result of constructive interference in the x-ray diffraction giving rise to bands of higher intensity. In this example, the periodicity 406 of the fibrils can give rise to the diffraction peaks, with each peak representing a different nearest neighbor distance. The intensity along the equatorial direction of diffraction pattern 403 can be taken from the center of the diffraction pattern to the edge and plotted as equatorial scattering profile 407. The equatorial scattering profile may comprise peaks 408 that can be related to the packing of the fibrils as well as the size of the fibrils. In this example, since the fibrils are packed at a larger distance than the diameter 409 of the fibrils, the peak from the packing may be at a lower q value (e.g., larger distance) than the peaks from the fibril size.

The image data, diffraction pattern data, or a combination thereof may undergo statistical analysis. The statistical analysis may comprise determination of a pair-wise distance distribution function, determination of a Patterson function, a calculation of a Porod invariant, a cluster analysis, a dispersion analysis, determination of one or more molecular structural periodicities, or any combination thereof. The pair-wise distance distribution function may be derived from the x-ray diffraction data. The pair-wise distance distribution function may be a distribution of neighbors to a scatterer (e.g., an atom, a fibril, etc.). For example, a pair-wise distribution function of an atomic lattice can show the distribution of nearest neighbors to the atom as a function of distance. In another example, a pair wise distribution function of collagen fibrils can show the probability of finding another collagen fibril as a function of distance from the first fibril. The pair-wise distance distribution function may provide information regarding the local structure around the scatterer. The Patterson function may provide information related to the phase component of an x-ray diffraction based on the intensity of the diffraction pattern. The Patterson function may provide information regarding the electron density of the local environment of the specimen. The Porod invariant may be a model independent invariant that may be used to determine a volume fraction of the sample. The Porod invariant may depend on the volume of the scatterer, but not the form. For example, a sphere of volume 1 cubic micron and a cube of volume 1 cubic micron can have a same value of the Porod invariant. The cluster analysis may be a statistical analysis of the diffraction data. The cluster analysis may determine a presence of one or more clusters in the data. For example, diffraction data can be analyzed to determine clusters of data based on one or more components of the data. The dispersion analysis may determine a dispersion of different types of features within the sample. For example, a dispersion analysis of the size of scattering fibrils can generate a distribution of the different sizes of fibrils in the sample. The dispersion analysis may determine the dispersion shape, dispersion width, dispersion modality (e.g., bimodal), or the like, or any combination thereof. The determination of one or more molecular structural periodicities may be a determination of the crystal structure of a molecular array. For example, the structure of a urea crystal within a sample can be determined. In another example, the structural periodicity of a light spot in a mammogram can be determined to identify the composition of the light spot. The determination of one or more molecular structural periodicities may provide an indicator of the identity of the molecule.

Figure 8:
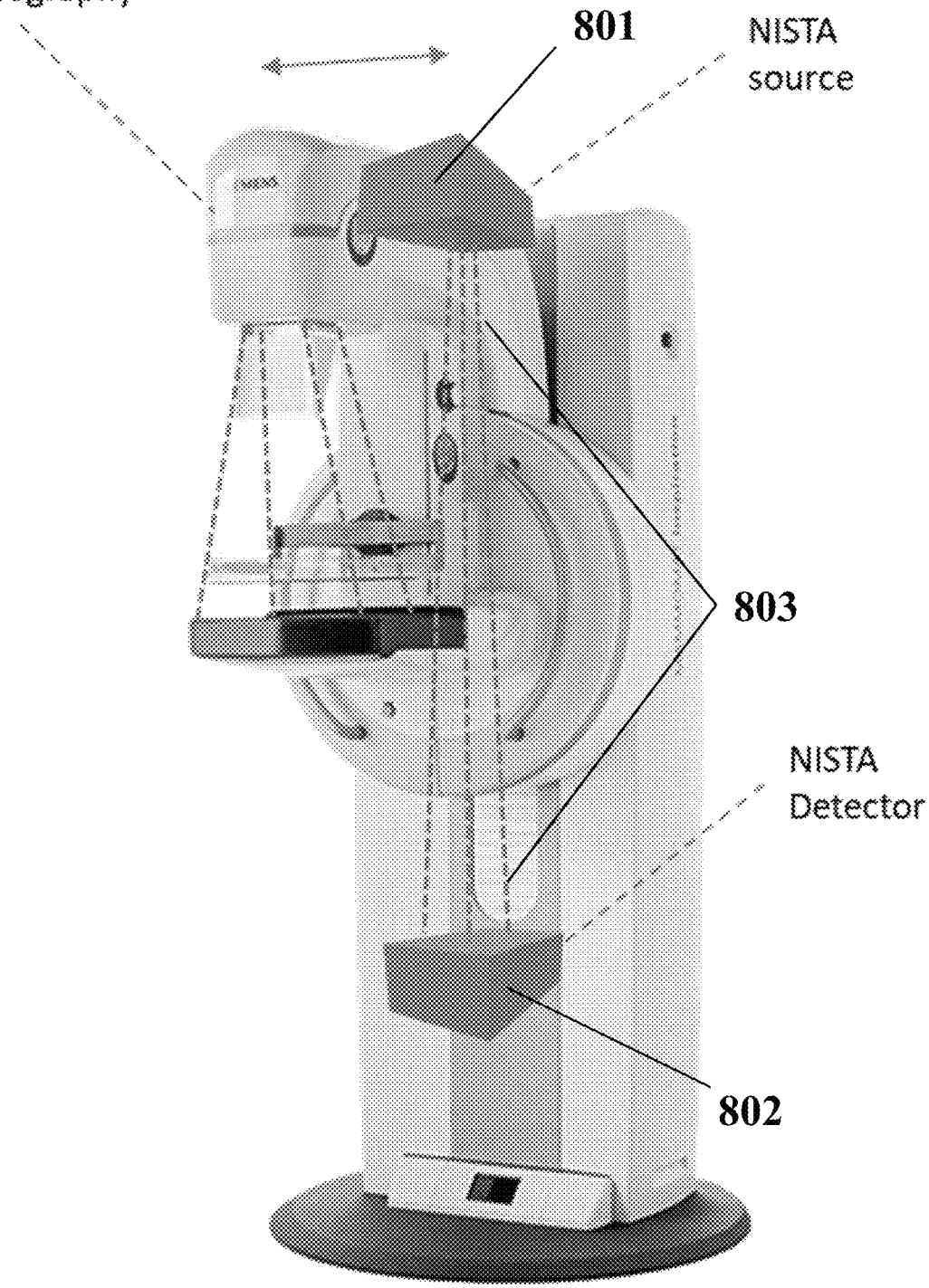
FIG. 8 shows an illustrative example of a combined mammography and x-ray diffraction instrument.

FIG. 8 shows an example of a combined mammography and x-ray diffraction instrument. The mammography portion of the instrument may be a mammography instrument made by a health instrumentation manufacturer (e.g., Siemens, GE, Philips). The mammography portion may use an x-ray source to project a beam of x-rays through a breast of a subject and measure the transmission of the x-rays. The transmission of the x-rays may be affected by a number of different factors, such as tissue density, tissue composition, presence of non-tissue species (e.g., calcium deposits), or the like. The x-ray source may be a radioisotope, an x-ray tube (e.g., a hot or cold cathode tube, a rotating anode tube, or the like), an x-ray laser, a plasma source, a synchrotron, a cyclotron, or the like. The x-ray source may generate collimated x-rays. The transmission of the x-rays may be detected by an x-ray detector as described elsewhere herein. The x-ray detector may be a film detector or a digital detector. The mammography portion of the instrument may be controlled by software. The software may comprise a user interface configured to display one or more mammography images to the subject and/or the healthcare provider. A healthcare provider may administer an x-ray contrast agent before taking a mammogram. For example, the healthcare provider can provide an iodine injection prior to taking the mammogram to aid in the visualization of blood vessels. The x-ray diffraction modality may provide strong signals in an absence of a contrast agent. For example, since the interaction between the x-ray beam and the tissue that produces the diffraction pattern can be independent of absorptive contrast, the diffraction pattern can be taken equally well with and without administering a contrast agent.

The x-ray diffraction modality may comprise an x-ray source 801 and an x-ray detector 802. The x-ray diffraction modality may be added to an existing mammography instrument (e.g., the x-ray diffraction modality is attached to a mammography instrument). The x-ray source may be an x-ray source as described elsewhere herein. The x-ray source may be a plurality of x-ray sources. For example, the x-ray source can comprise a high energy x-ray source and a low-energy x-ray source. In this example, the x-ray source can be selected based on the properties of the x-rays that can generate the optimal diffraction data. The x-ray source may generate a plurality of x-ray beams. The x-ray detector may be an x-ray detector as described elsewhere herein. The x-ray detector may be a plurality of x-ray detectors. One or more optical elements may be placed in the beam path 803 between the x-ray source and the x-ray detector. The one or more optical elements may be one or more phase plates, beam shaping elements (e.g., slits), diffraction gratings, single crystals, lenses, gratings, phosphor layers, power meters, or the like, or any combination thereof. The x-ray source and/or the x-ray detector may be movable. For example, the x-ray detector can be movable between two different distances from the x-ray source to change from a SAXS mode to a WAXS mode. The x-ray detector, x-ray source, one or more optical elements, or any combination thereof, may be configured to be controlled by one or more computer processors. The one or more computer processors may control the x-ray source by programming a voltage and/or a current for the source, controlling a shutter state, selecting an x-ray source from a plurality of x-ray sources, or the like, or any combination thereof. The one or more computer processors may control the one or more optical elements by adjusting a position of the one or more optical elements (e.g., moving a lens, changing a width of an adjustable slit), changing a phase of a phase plate, adjusting a transmission of a variable filter, or the like, or any combination thereof. The one or more computer processors may control the x-ray detector by programming a binning of the detector, setting an exposure time of the detector, selecting an active detector, adjusting parameters of the detector (e.g., gain, contrast, gamma), or the like, or any combination thereof. One or more visible light sources (e.g., lasers) may be used to show where the one or more x-ray beams will interact with the tissue.

Figure 9:
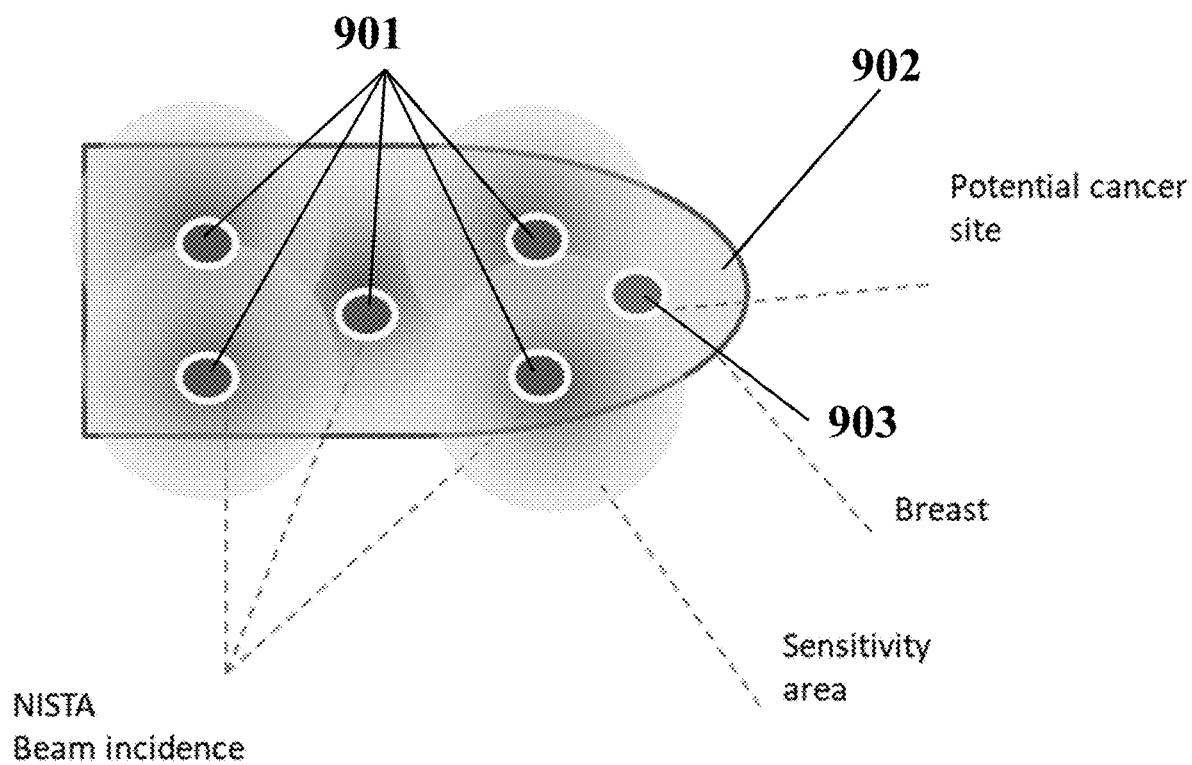
FIG. 9 shows an example top view of a breast being probed by an x-ray diffraction system.

FIG. 9 shows an example top view of a breast being probed by an x-ray diffraction system. Points 1001 can be locations of incident x-ray beams on breast 1002. The incident x-ray beam may be a plurality of incident x-ray beams. The incident x-ray beams may be configured to generate diffraction pattern data around each point as shown by the circular sensitivity areas around each point. For example, the diffraction pattern data can be sensitive within 2 inches around the x-ray beam. The sensitivity areas of some of the x-ray beams can overlap with a potential cancer site 1003. Since the sensitivity area overlaps the potential cancer site, diffraction data indicative of the presence or absence of the cancer can be generated. By projecting a plurality of beams through a tissue (e.g., a breast), the entire tissue may be tested for a presence of an abnormality. In the example of FIG. 9, the five beams can generate signals indicative of the presence of a cancer at the potential cancer site 1003. In this example, the presence of the signal can lead to a determination of an approximate position of the cancer, which can allow for more detailed investigation. The diffraction pattern data may be processed. The processing may comprise intensity normalization, calibration, glitch removal, detector dead time correction, scaling, baselining, or the like, or any combination thereof. The processing may comprise applying one or more machine learning algorithms to the diffraction pattern data. For example, the points that are far from the potential cancer site may be used as control regions, while the points nearer to the potential cancer site can be analyzed for the presence or absence of the cancer. The x-ray beams may interact with the tissue at a same time as an absorptive mammography image is taken.

Figure 10:
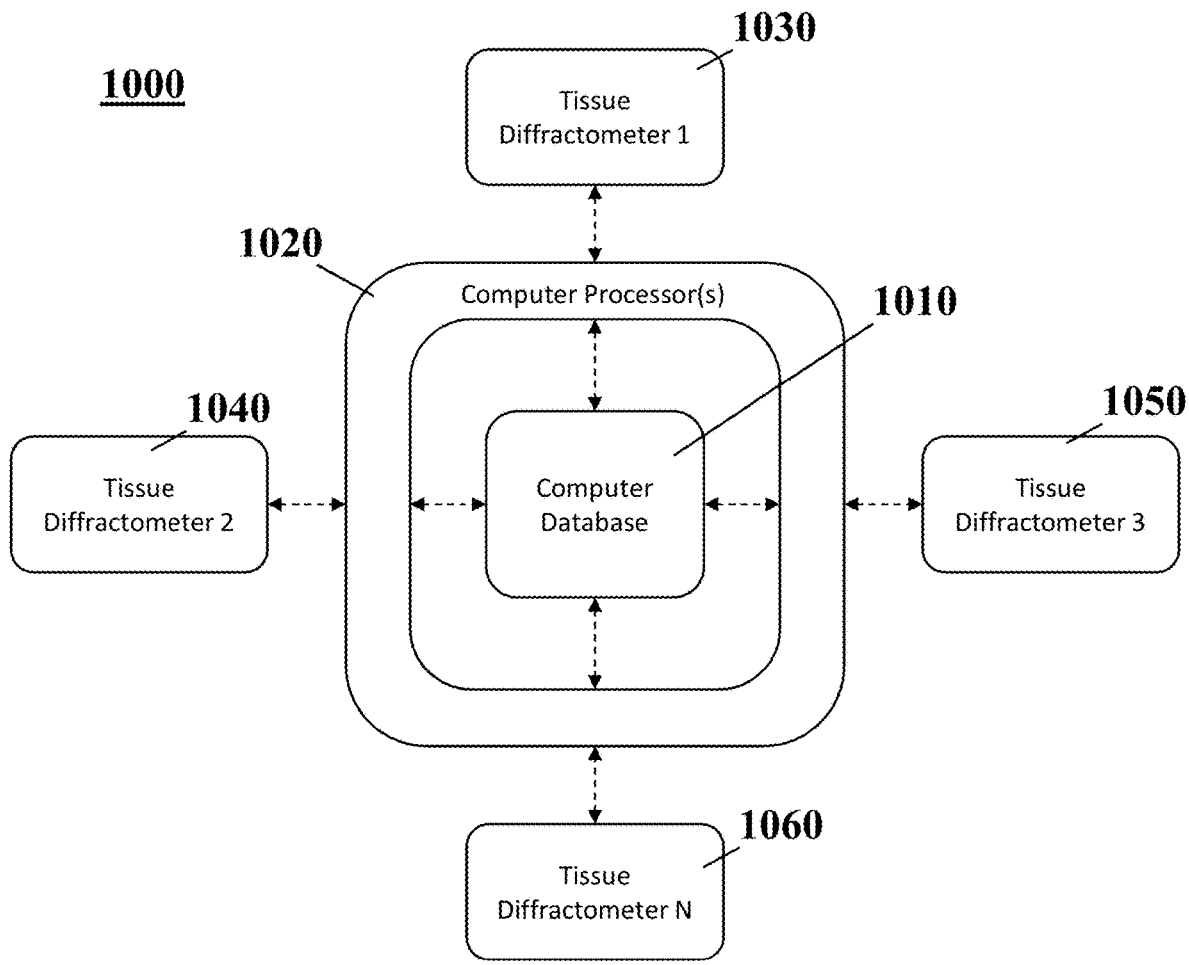
FIG. 10 shows a schematic of a plurality of tissue diffractometers operatively coupled to a computer database over a network.

FIG. 10 shows a schematic of a plurality of tissue diffractometers operatively coupled to a computer database over a network. The plurality of tissue diffractometers operatively coupled to the computer database over the network may be a global diagnostics system 1000. The global diagnostics system may comprise a computer database 1010. The computer database may be configured to store data (e.g., image data, diffraction pattern data, subject data, or any combination thereof). The central computer database may be encrypted. The computer database may be configured for compliance with health data privacy laws and regulations (e.g., HIPAA). The computer database may be a distributed computer database (e.g., a cloud-based database housed at a plurality of locations). The computer database may be configured to accept data from one or more tissue diffractometers 1030, 1040, 1050, and/or 1060 via one or more computer processor(s) 1020. The one or more computer processors may be configured to pre-process, process, and/or post-process the data as described elsewhere herein. The one or more computer processors may be coupled to the one or more tissue diffractometers via a network (e.g., a local network, the internet, a virtual private network). The one or more tissue diffractometers may be at least about 1, 5, 10, 25, 50, 75, 100, 250, 500, 750, 1,000, 2,500, 5,000, 10,000, 50,000, 100,000 or more tissue diffractometers. The one or more tissue diffractometers may be at most about 100,000, 50,000, 10,000, 5,000, 2,500, 1,000, 750, 500, 250, 100, 75, 50, 25, 10, 5, or less tissue diffractometers. The one or more tissue diffractometers may be one or more of a same type of tissue diffractometer (e.g., a same model), or one or more of a different type of tissue diffractometers (e.g., one or more different models of tissue diffractometers). The computer processors 1020 may be configured to periodically refine and update a statistical and/or machine learning based data analytics algorithm using data stored in the computer database 1010. For example, the data analytics algorithm may be updated every month, every week, every day, or every hour. In some instances, the computer processors 1020 and computer database 1010 may be configured to continually refine a statistical and/or machine learning based data analytics algorithm. For example, each time new data is received from a tissue diffractometer, the computer processors 1020 can access that new data from the computer database 1010 to update the data analytics algorithm. The data analytics algorithm may be a data analytics algorithm and/or machine learning algorithm as described elsewhere herein.

Figure 11:
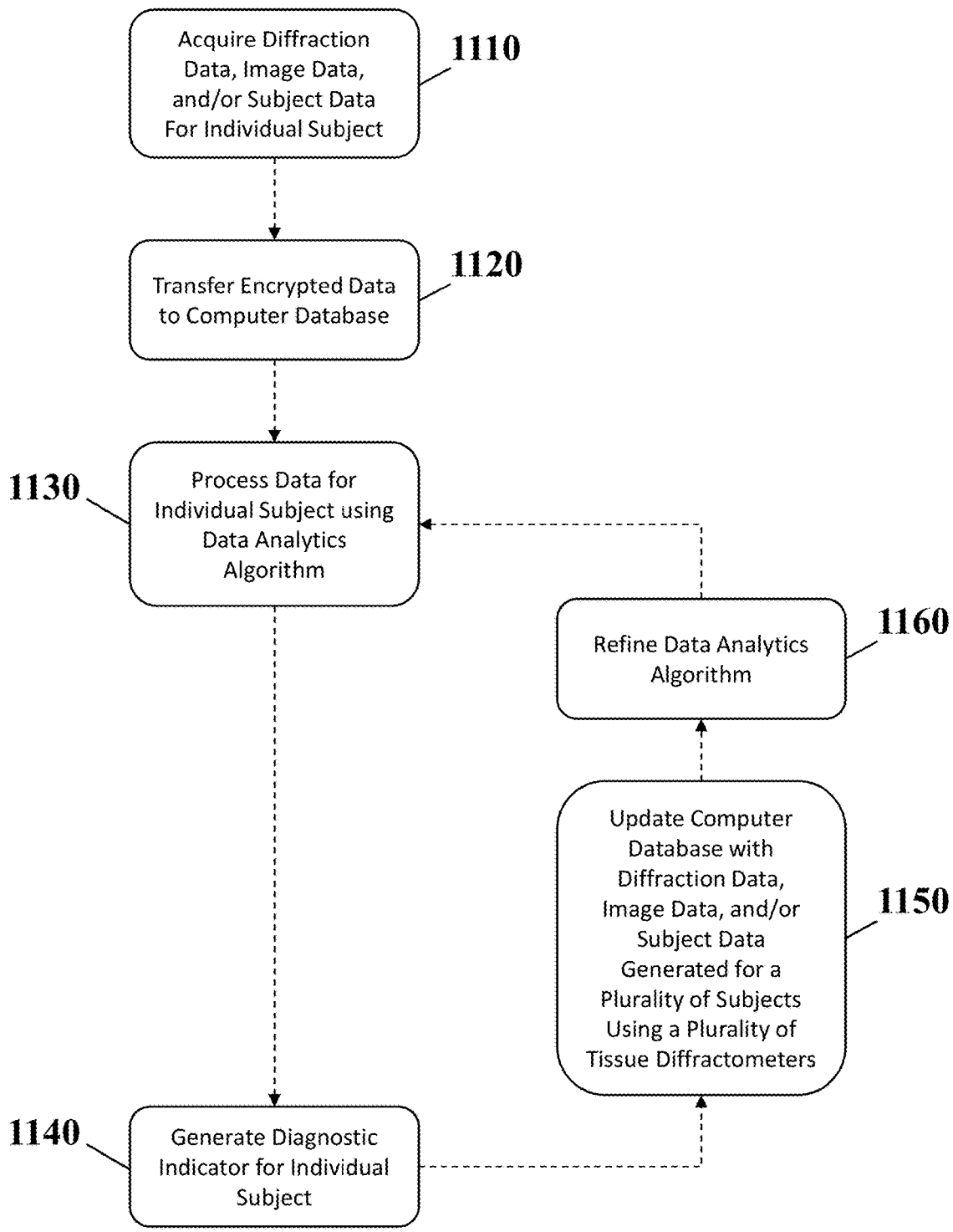
FIG. 11 shows an example schematic for a data collection and processing workflow.

FIG. 11 shows an example schematic for a data collection and processing workflow 1100. In an operation 1110, the process 1100 may comprise acquiring diffraction data, image data, subject data, or any combination thereof for an individual subject. The acquiring may be acquiring using an absorptive mammography instrument, a diffraction-based instrument, or a combination thereof. For example, a combined mammography and diffraction instrument can acquire both absorptive mammography images and tissue diffraction patterns. The acquiring may be in a single session. For example, subject data comprising medical history and ancestral medical information can be acquired through an interview with the subject before a mammogram is taken. The acquiring may be over a plurality of sessions. For example, a time series of mammography images and diffraction patterns can be taken over a period of time to track a change in a cancer state of a subject. The image data, diffraction data, subject data, or any combination thereof may be data as described elsewhere herein. The acquiring may be performed by one or more tissue diffractometers as described elsewhere herein.

In another operation 1120, the process 1100 may comprise transferring encrypted data to a computer database. The encrypted data may comprise image data, diffraction pattern data, subject data, or any combination thereof for one or more individual subjects. For example, the encrypted data can comprise all of the data taken from a radiology clinic in a day. In another example, the encrypted data can be data from an individual subject served by a radiology clinic. The encrypted data may be encrypted using an asymmetric key encryption, a symmetric key encryption, or the like. The encrypted data may be encrypted by a computing device local to where the data was generated (e.g., a computer operatively coupled to a tissue diffractometer). The encrypted data may be stored locally before being transferred to the computer database. The encrypted data may be streamed (e.g., transferred in real-time or substantially real-time) to the computer database. The computer database may be a local computer database (e.g., a local computing cluster housed in the same facility as where the data was acquired) or a remote computer database (e.g., a cloud computing database). The encrypted data may be uncompressed data or compressed data.

In another operation 1130, the process 1100 may comprise processing data for the individual subject using a data analytics algorithm. The processing may be performed on one or more computer processors as described elsewhere herein. The processing may be encoded on a non-transitory computer readable medium. The data analytics algorithm may be a statistical analysis algorithm and/or a machine learning algorithm. The data analytics algorithm may be a convolutional neural network as described elsewhere herein. The data analytics algorithm may perform pre-processing, processing, and/or post-processing of diffraction data, image data, subject data, or any combination thereof. The pre-processing may comprise denoising (e.g., removing nose from the data), normalizing (e.g., standardizing data properties such as size, black level, maximum intensity, etc.), segmentation (e.g., dividing the data into sections comprising different features), masking (e.g., applying one or more masks to the data), enhancing edges and/or features, or the like, or any combination thereof. The processing may comprise determining a presence or absence of a feature in the data (e.g., determining a presence of a cancerous spot in a mammography image by in part using a breast tissue diffraction pattern), determining a severity of a feature in the data (e.g., determining the progression of a cancer), clustering data (e.g., clustering images based on the presence or absence of a feature), predicting a presence or absence of a feature in new data (e.g., using previously acquired images to generate a prediction of a presence of a feature in a new set of data), or the like, or any combination thereof. The post-processing may comprise formatting (e.g., formatting data for presentation to a subject or a healthcare worker), denoising, normalizing, masking, enhancing properties (e.g., contrast, edges), or the like, or any combination thereof.

In another operation 1140, the process 1100 may comprise generating a diagnostic indicator for the individual subject. The diagnostic indicator may be a quantitative diagnostic indicator. The computer aided diagnostic indicator may be a computer readable report, a human readable report, or both. For example, the computer aided diagnostic indicator can be a report displayed on a user interface of a device. The diagnostic indicator may comprise information about a likelihood of a presence of a feature in the data (e.g., a presence of breast cancer in mammography and diffraction data), a severity of a presence of a feature (e.g., a prognosis based on the severity of the feature), one or more suggested treatments (e.g., a suggestion of a mastectomy for a severe breast cancer), additional information (e.g., locations of resources to help the subject understand the diagnostic indicator), subject data (e.g., the name of the subject the indicator is for), or the like, or any combination thereof. The diagnostic indicator may be generated on a same computer system as the data analytics algorithm was run on. The diagnostic indicator may be held until the subject or the healthcare provider provides an input. The input may be a payment (e.g., a payment from the subject, a payment from the subject's insurance), an agreement for the subject's data to be used for training and/or validating future data analytics algorithms, or the like, or any combination thereof. For example, the subject can be informed that the diagnostic indicator is ready, and that the subject can sign a waiver allowing use of the subject's data.

In another operation 1150, the process 1100 may comprise updating the computer database with the image data, diffraction data, subject data, or any combination thereof generated for a plurality of subjects using a plurality of tissue diffractometers. The updating may make additional data available to train a new data analytics algorithm or update an existing data analytics algorithm. The computer database may be updated with indicators of a confirmation of an indication made in a diagnostic indicator. For example, the database can be updated with information regarding the surgical confirmation of cancer in a patient for whom the diagnostic indicator indicated a likelihood of cancer. This updating may provide a confirmation of positive or negative results that can improve the accuracy of future diagnostic indicators. The data may be agglomerated for the plurality of subjects to generate a general classifier. For example, a database of breast images and diffraction patterns can be used to generate a classifier for breast tissue. In another example, a database of brain images and diffraction patterns can be used to generate a classifier for brain tissues.

In another operation 1160, the process 1100 may comprise refining the data analytics algorithm. The refining may comprise generating a new data analytics algorithm. The refining may comprise an updating of weights or other components within the data analytics algorithm. For example, the neural weights of a neural network can be updated based on the additional data from the plurality of subjects. The refining of the data analytics algorithm may improve the sensitivity, specificity, accuracy, or any combination thereof of the data analytics algorithm. The refined data analytics algorithm may be used to process the data for another subject (e.g., used as the data analytics algorithm of operation 1130).

The methods and systems of the present disclosure may be applied for diagnostic purposes. For example, the presence of a cancer in a breast of a subject can be diagnosed using a combination of mammography and diffraction pattern data. The diagnostic purposes may include cancer diagnosis, muscular condition diagnoses (e.g., muscular degeneration), optometric diagnoses (e.g., corneal damage, other eye diseases), bone condition diagnoses (e.g., osteoporosis), other tissue diagnoses (e.g., brain degeneration), or the like, or any combination thereof. The generation of diffraction pattern data may be combined with mammography instruments, chest x-ray instruments, skull x-ray instruments, limb x-ray instruments, C-arm x-ray instruments, or the like. For example, a C-arm x-ray instrument can comprise two optical paths, one for absorptive imaging and another for diffraction pattern data generation.

Figure 12:
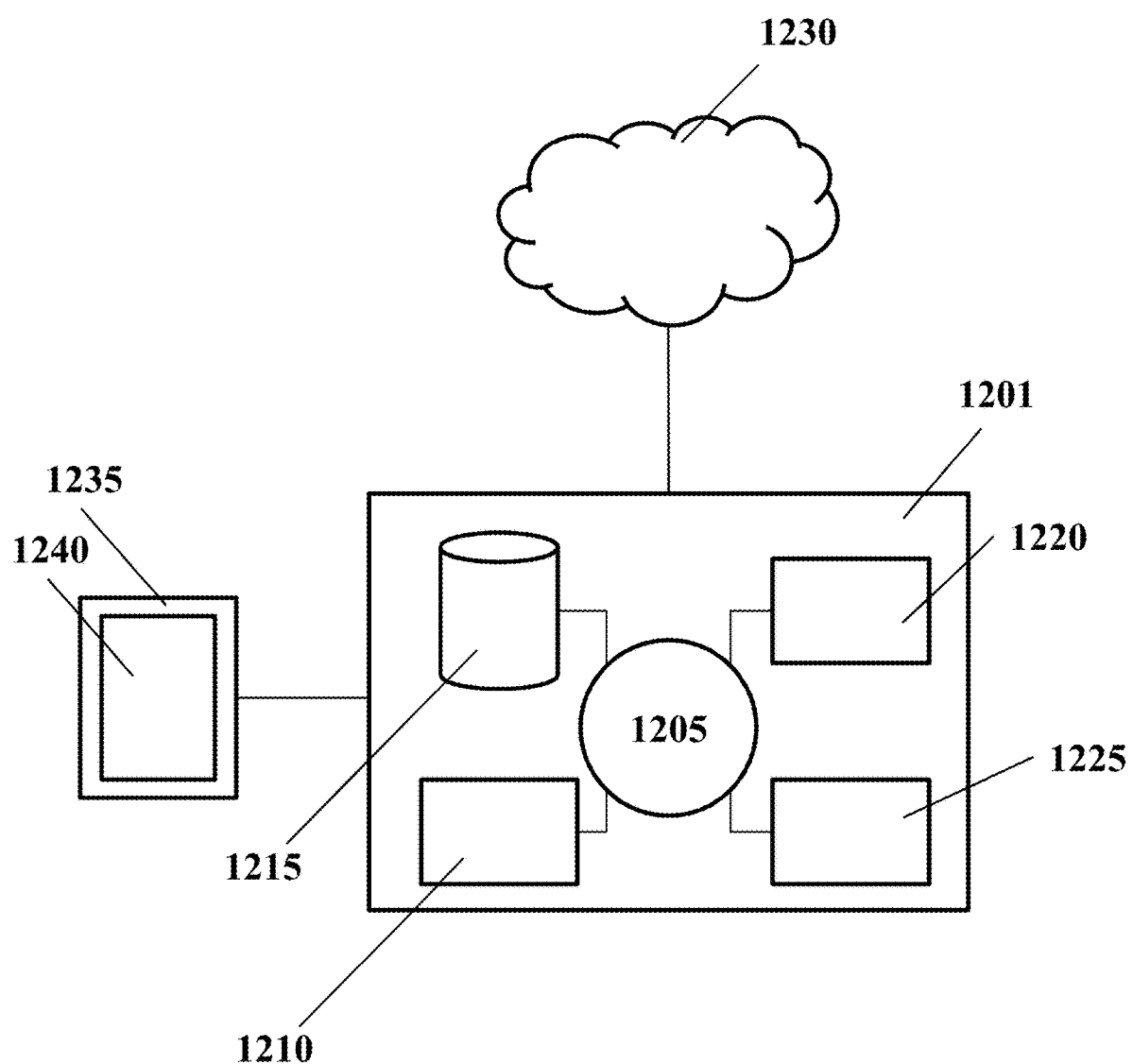
FIG. 12 shows a computer system that is programmed or otherwise configured to implement methods provided herein.

The present disclosure also provides computer systems that are programmed to implement methods of the disclosure. FIG. 12 shows a computer system 1201 that is programmed or otherwise configured to implement methods described elsewhere herein (e.g., obtaining data from one or more tissue diffractometers, processing the data, etc.). The computer system 1201 can regulate various aspects of the present disclosure, such as, for example, the processing of image data, diffraction pattern data, subject data, or any combination thereof. The computer system 1201 can be an electronic device of a user or a computer system that is remotely located with respect to the electronic device. The electronic device can be a mobile electronic device. The computer system 1201 may be a post-classical computer system (e.g., a quantum computing system).

The computer system 1201 includes a central processing unit (CPU, also "processor" and "computer processor" herein) 1205, which can be a single core or multi core processor, or a plurality of processors for parallel processing. The computer system 1201 also includes memory or memory location 1210 (e.g., random-access memory, read-only memory, flash memory), electronic storage unit 1215 (e.g., hard disk), communication interface 1220 (e.g., network adapter) for communicating with one or more other systems, and peripheral devices 1225, such as cache, other memory, data storage and/or electronic display adapters. The memory 1210, storage unit 1215, interface 1220 and peripheral devices 1225 are in communication with the CPU 1205 through a communication bus (solid lines), such as a motherboard. The storage unit 1215 can be a data storage unit (or data repository) for storing data. The computer system 1201 can be operatively coupled to a computer network ("network") 1230 with the aid of the communication interface 1220. The network 1230 can be the Internet, an internet and/or extranet, or an intranet and/or extranet that is in communication with the Internet. The network 1230 in some cases is a telecommunication and/or data network. The network 1230 can include one or more computer servers, which can enable distributed computing, such as cloud computing. The network 1230, in some cases with the aid of the computer system 1201, can implement a peer-to-peer network, which may enable devices coupled to the computer system 1201 to behave as a client or a server.

The CPU 1205 can execute a sequence of machine-readable instructions, which can be embodied in a program or software. The instructions may be stored in a memory location, such as the memory 1210. The instructions can be directed to the CPU 1205, which can subsequently program or otherwise configure the CPU 1205 to implement methods of the present disclosure. Examples of operations performed by the CPU 1205 can include fetch, decode, execute, and writeback.

The CPU 1205 can be part of a circuit, such as an integrated circuit. One or more other components of the system 1201 can be included in the circuit. In some cases, the circuit is an application specific integrated circuit (ASIC).

The storage unit 1215 can store files, such as drivers, libraries and saved programs. The storage unit 1215 can store user data, e.g., user preferences and user programs. The computer system 1201 in some cases can include one or more additional data storage units that are external to the computer system 1201, such as located on a remote server that is in communication with the computer system 1201 through an intranet or the Internet.

The computer system 1201 can communicate with one or more remote computer systems through the network 1230. For instance, the computer system 1201 can communicate with a remote computer system of a user (e.g., a cloud server). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1201 via the network 1230.

Methods as described herein can be implemented by way of machine (e.g., computer processor) executable code stored on an electronic storage location of the computer system 1201, such as, for example, on the memory 1210 or electronic storage unit 1215. The machine executable or machine-readable code can be provided in the form of software. During use, the code can be executed by the processor 1205. In some cases, the code can be retrieved from the storage unit 1215 and stored on the memory 1210 for ready access by the processor 1205. In some situations, the electronic storage unit 1215 can be precluded, and machine-executable instructions are stored on memory 1210.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1201, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1201 can include or be in communication with an electronic display 1235 that comprises a user interface (UI) 1240 for providing, for example, an interface for a healthcare or an individual subject to upload image data, diffraction pattern data, subject data, or any combination thereof to a computer database. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1205. The algorithm can, for example, be a machine learning algorithm as described elsewhere herein.

EXAMPLES

The following examples are illustrative of certain systems and methods described herein and are not intended to be limiting.

Example 1 X-Ray Diffraction Measurements of Breast Tissue

Figure 5A:
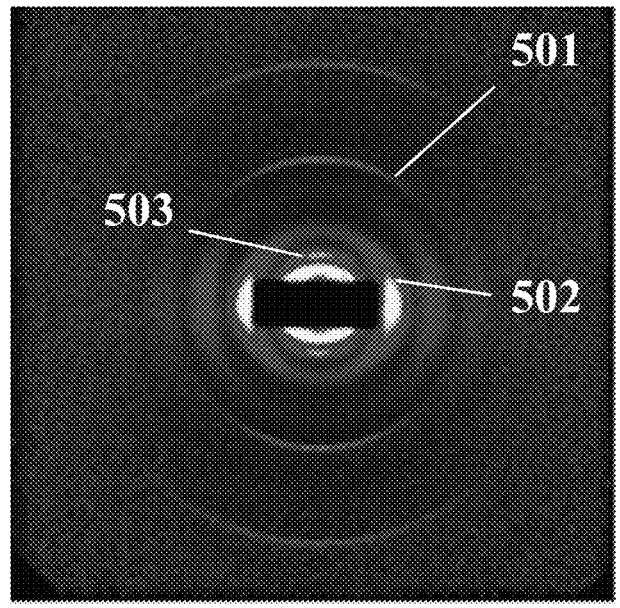
FIGS. 5A-5B show examples of small angle x-ray (SAXS) diffraction data.
Figure 5B:
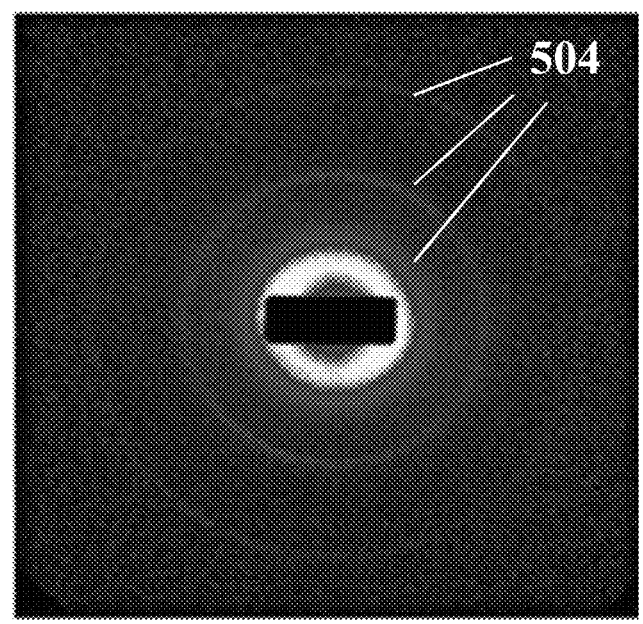

FIGS. 5A-5B show examples of small angle x-ray diffraction data. The normal tissue diffraction pattern of FIG. 5A exhibits clear peaks in the diffraction pattern, such as those called out as y-axis peak 501 and x-axis peak 502. The asymmetry of the size and distance of peaks 501 and 502 can be indicative of different size domains in each direction. Because the 2D diffraction pattern is in q space (e.g., with a dimension of 1/nm), the peak 501 can be indicative of shorter-range ordering as compared to peak 502 at lower q and thus larger range. The presence of diffraction spots 503 can be indicative of a presence of highly ordered and homogenous patterns (e.g., lines, lattices of points) within the tissue. Based on this diffraction pattern, the presence of asymmetric long- and short-range ordering can be an indicator of healthy breast tissue, such as a presence of uninterrupted collagen in the tissue or the presence of undisturbed fibrils. In contrast, the diffraction pattern of FIG. 5B, which was taken of breast tissue with a known disease, shows weak, symmetric diffraction peaks 504. As compared to the peaks in FIG. 5A, peaks 504 are weak and do not demonstrate asymmetric ordering. This is because the disease in the breast tissue results in a disruption of the tissue and a destruction of long-range order. For example, the tissues of FIGS. 3A-3B show the difference between healthy, ordered tissues and unhealthy, disordered tissues that can give rise to diffraction patterns as seen in FIGS. 5A-5B.

Figure 6A:
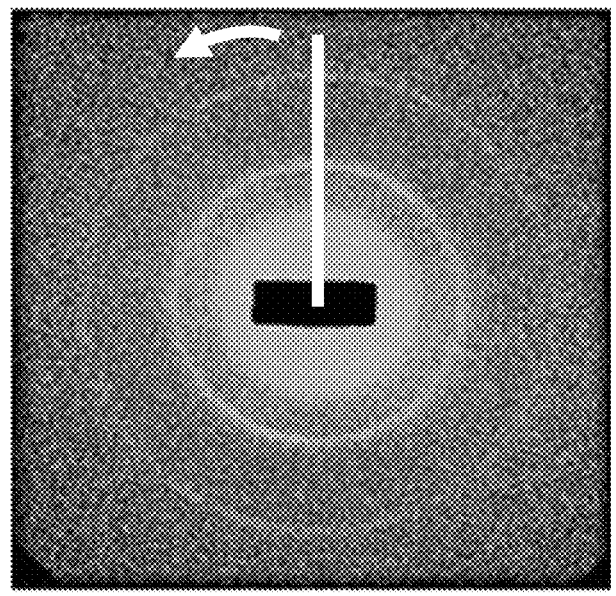
FIGS. 6A-6B show examples of small angle x-ray diffraction data from a breast tissue with a known disease.
Figure 6B:
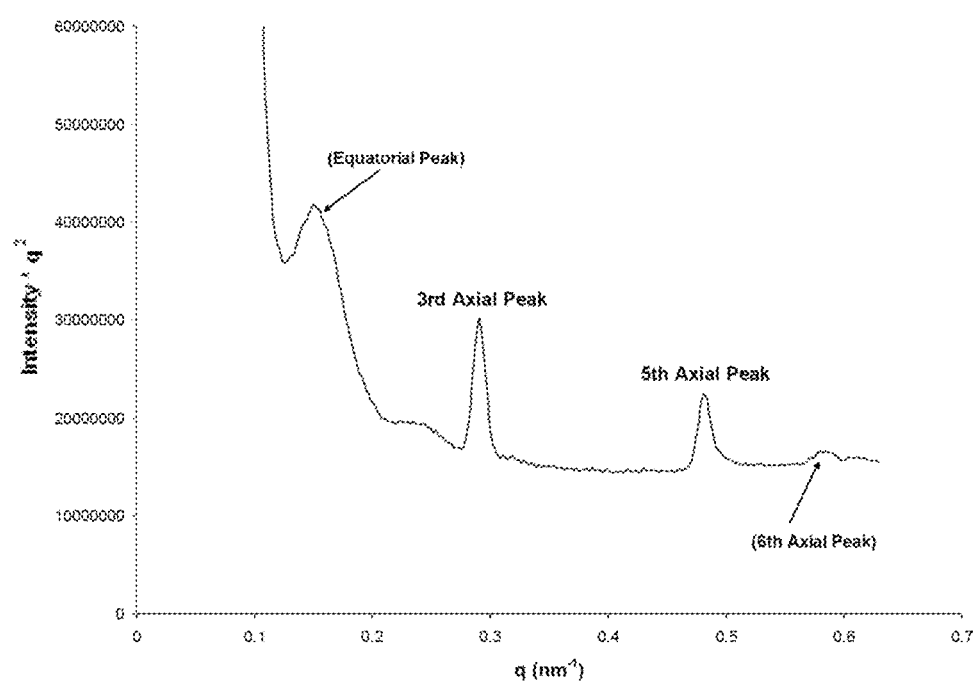

FIGS. 6A-6B show examples of small angle x-ray diffraction data from a breast tissue with a known disease. The diffraction pattern of FIG. 6A can be radially integrated (e.g., a slice of the image can be taken and rotated about the center as shown on the figure) to generate a 2D diffraction pattern as seen in FIG. 6B. Each of the high intensity regions of FIG. 6A can give rise to a peak in the diffraction pattern of FIG. 6B. While radially integrating can remove information about a distribution of the signals between axial and equatorial components, it can also improve signal to noise and provide a convenient way to display diffraction data. Additionally, knowing the approximate q value of the peak from the diffraction image can enable tracking of the peak in the diffraction pattern, as one can relate the q position from the image to a peak in the integrated pattern. The diffraction pattern of FIG. 6B is read where the center of the diffraction image corresponds to the far left of the pattern, and larger q corresponds to the edges of the diffraction image. Since q is in units of inverse space, the higher q peaks correspond to smaller spacings. For example, the fifth axial peak of FIG. 6B corresponds to an ordering with a feature size of approximately 0.5 inverse nanometers. The intensities of the peaks, as well as the position, width (e.g., full width at half maximum), shape (e.g., gaussian shape, Lorentzian shape), or any combination thereof can be indicators of the order state of the tissue, which can be related to a presence or absence of a disease. Diffraction images such as that of FIG. 6A, as well as diffraction patterns such as that of FIG. 6B can be used as input data for a machine learning algorithm configured to detect a presence or absence of a cancer.

Figure 7:
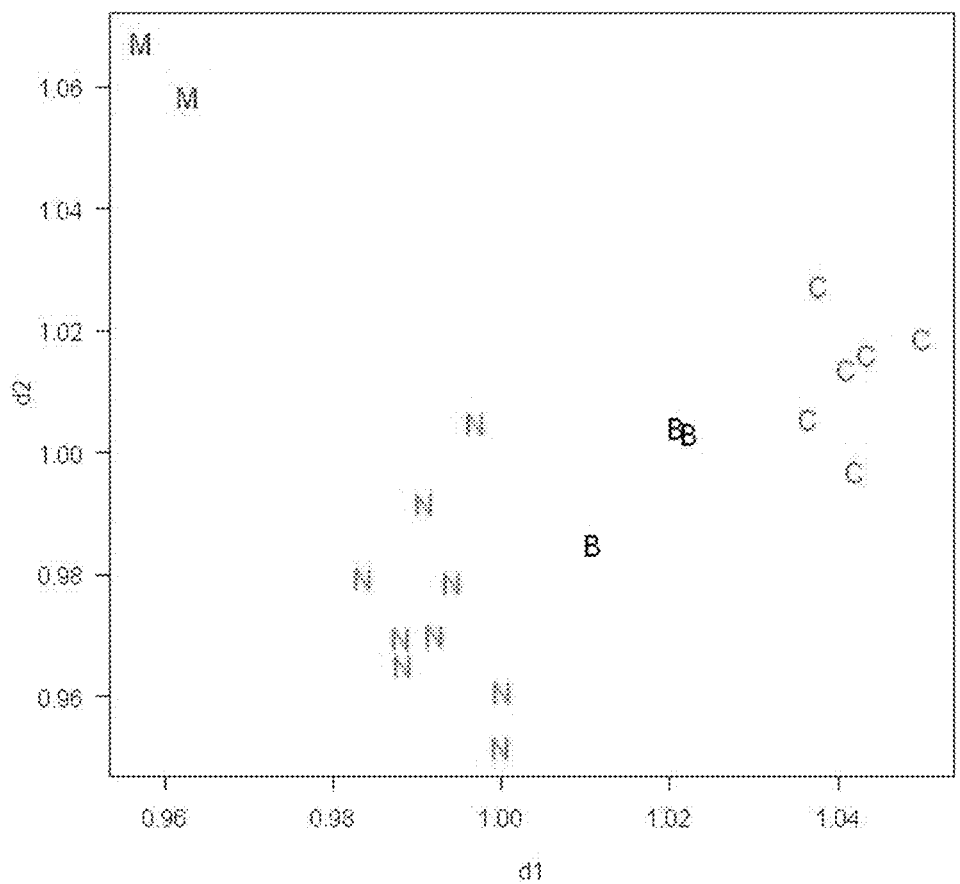
FIG. 7 shows an example of data extracted from x-ray diffraction patterns that has been plotted to illustrate the clustering for different tissue types (from: "Small Angle X-Ray Scattering as a Diagnostic Tool for Breast Cancer", Sabeena Sidhu, BSc, MSc School of Physics, Monash University, Feb. 12, 2009).

FIG. 7 shows an example of data extracted from x-ray diffraction patterns that has been plotted to illustrate the clustering for different tissue types. In this example, the intensity of two peaks, d1 and d2, in a plurality of datasets were plotted against each other to form the scatter plot. A convolutional neural network can then process the data to cluster the points based not only on the relative intensities of the two peaks, but also based on other data from the diffraction patterns and related mammography data. The neural network can then assign indicators to each of the clusters to aid in a diagnosis. In this example, the clusters were labeled as non-cancerous (N), malignant (M), suspicious (B), and indicative of calcium deposits (C). In an example, a new diffraction pattern is processed and shows a d1 peak intensity of 0.91 and a d2 peak intensity of 1.05. In this example, the new diffraction pattern can be classified as being of a malignant breast sample, as the new data fits best with the malignant cluster. The neural network can then be updated with the new data to improve the effectiveness of the neural network for future data.

Another application of the disclosed methods and systems is monitoring of therapeutic efficacy for cancer treatments or disease therapeutics (e.g., drugs). Subjects (e.g., patients) may undergo one or more follow up examinations at various time points following the initiation of, during treatment by, or after completion of a therapeutic treatment, and the clustering of data derived from the analysis of image data, diffraction data, subject data, or any combination thereof, is analyzed and re-evaluated for changes in sample data characteristics and clustering. As a result, the data analytics algorithm may, for example, plot patient sample data points in an n-dimensional space defined by two or more treatment parameters that describe the clustering of the sample data, and the distance or changes in distance between different clusters may be calculated as a function of time. In some instances, for example, the proximity of a new data point to the previous data point(s), or the trajectory of certain data clusters (or the gradient of the trajectory) may be used as an indicator for the therapy's effectiveness and can be interpreted by physician in terms of therapeutic efficiency. In some instances, the output of the data analytics algorithm (e.g., a quantitative diagnostic indicator) generated for multiple examinations may be used directly to monitor the efficacy of a therapeutic treatment. Comparing the results of follow up assessments for multiple patients' samples may provide indications of the efficiency of certain drugs and treatments in specific groups of patients.

The invention may also be described by the following numbered paragraphs:

1. A method of in vivo human-tissue analysis and communication that produces a quantitative diagnostic indicator for human-tissue, comprising: analyzing human tissue and producing an quantitative-diagnostic indicator; and sending and receiving information relevant to the quantitative-diagnostic indicator.
2. The method of paragraph 1, further including the steps of operatively coupling at least one tissue diffractometer to a computer database over a network, and acquiring human-tissue data chosen from the group consisting of in situ image data, in situ diffraction pattern data, and subject data, and transfer of the human-tissue data to the computer database over the network.
3. The method of paragraph 2, further including the steps of operatively coupling at least one computer processor to the at least one tissue diffractometer, and configuring the at least one computer processor to receive the human-tissue data from the at least one diffractometer, transmit the human-tissue data to the computer database; and process the human-tissue data using a data analytics algorithm that provides a quantitative-diagnostic indicator of human tissue.
4. The method of paragraph 3, further including the steps of operatively coupling the at least one tissue diffractometer to a computer database over a network, and configuring the computer database for acquisition and transfer of data from the data group consisting of in situ image data, in situ diffraction pattern data, and subject data, to the computer database over the network.
5. The method of paragraph 4, further including the steps of operatively coupling the at least one computer processor to the at least one tissue diffractometer, and configuring the at least one computer processor to (i) receive data from the data group; (ii) transmit data from the data group; and (iii) process the data from the data group for a human subject using a data analytics algorithm that provides a quantitative diagnostic indicator for the human subject.
6. The method of paragraph 5, further including the steps of providing a user interface that allows a human subject's data from the data group to be uploaded to the computer database in exchange for processing of the subject's data to receive the quantitative diagnostic indicator for the subject.
7. The system of paragraph 6, further including the steps of configuring the user interface to allow a human subject or their healthcare provider to make payments or upload a human subject's signed consent form.
8. The method of paragraph 2, wherein the at least one tissue diffractometer comprises two or more tissue diffractometers, each located in different geographic locations.
9. The method of paragraph 8, wherein the plural tissue diffractometers comprise a data encryption device that includes a global positioning system (GPS) positioning sensor and generates encrypted data, and the encrypted data transferred to the computer database track changes in locations of the plurality of tissue diffractometers.
10. The method of paragraph 9, wherein the plural tissue diffractometers are configured to perform small angle X-ray scattering (SAXS) measurements.
11. The method of paragraph 9, wherein the plural tissue diffractometers are configured to perform wide angle X-ray scattering (WAXS) measurements.
12. The method of paragraph 9, wherein the plural tissue diffractometers are further configured to perform mammography.
13. The method of paragraph 10, wherein a set of target coordinates for directing an X-ray beam are determined from a mammogram.
14. The method of paragraph 2, wherein the computer database resides on a central server.
15. The method of paragraph 2, wherein the computer database resides in the cloud.
16. The method of paragraph 4, further including the step of depersonalizing the data from the data group prior to transferring it to the computer database.
17. The method of paragraph 16, wherein a key for mapping the depersonalized data stored in the computer database to the human subject is stored in a local institutional database or in the human subject's personal files.
18. The method of any one of paragraph 5, wherein the data analytics algorithm comprises a statistical analysis of diffraction pattern data or a function thereof 19. The method of paragraph 18, wherein the statistical analysis comprises determination of a pair-wise distance distribution function, determination of a Patterson function, a calculation of a Porod invariant, a cluster analysis, a dispersion analysis, determination of one or more molecular structural periodicities, or any combination thereof.

20. The method of paragraph 19, wherein the statistical analysis comprises a determination of a structural periodicity of collagen.

21. The method of paragraph 19, wherein the statistical analysis comprises a determination of a structural periodicity of a lipid.

22. The method of paragraph 19, wherein the statistical analysis comprises a determination of a structural periodicity of a tissue.

23. The method of paragraph 5, wherein the data analytics algorithm comprises a machine learning algorithm.

24. The method of paragraph 23, wherein the machine learning algorithm comprises a supervised learning algorithm, an unsupervised learning algorithm, a semi-supervised learning algorithm, a reinforcement learning algorithm, a deep learning algorithm, or any combination thereof 25. The method of paragraph 24, wherein the machine learning algorithm is a deep learning algorithm.

26. The method of paragraph 25, wherein the deep learning algorithm is a convolutional neural network, a recurrent neural network, or a recurrent convolutional neural network.

27. The method of paragraph 24, wherein the machine learning algorithm is trained using a training dataset comprising in situ image data, in situ diffraction pattern data, subject data, or any combination thereof stored in the computer database for a specific pathology or physiological norm group.

28. The method of paragraph 27, wherein the training dataset is updated as new data from the data group.

29. The method of paragraph 28, wherein the subject data comprises a human subject's age, sex, ancestry data, genetic data, behavioral data, or any combination thereof 30. The method of paragraph 29, wherein the quantitative diagnostic indicator for the human subject comprises an indicator of the likelihood that the human subject has cancer.

31. The method of paragraph 30, wherein the indicator of the likelihood that the human subject has cancer is an indicator of the likelihood that the human subject has breast cancer.

32. The method of paragraph 30, wherein the quantitative diagnostic indicator for the human subject comprises a diagnosis that the human subject has cancer.

33. The method of paragraph 32, wherein the diagnosis that the human subject has cancer is a diagnosis that the human subject has breast cancer.

33. The method of paragraph 2, further comprising repeating the steps of the method one or more subsequent times to monitor a disease state of the human subject as the human subject undergoes a therapeutic treatment.

34. The method of paragraph 33, wherein a rate of change of the disease state of the human subject as indicated by the quantitative diagnostic indicator provides a measure of the efficacy of the therapeutic treatment.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed:

1. An in vivo human-tissue analysis and communication system that produces a diagnostic indicator for human tissue analyzed by the system, comprising:
    at least one computer processor operatively coupled to a tissue diffractometer and to a computer database over a network, wherein the at least one computer processor is configured for acquisition of human tissue data, wherein the human tissue data is chosen from a data group consisting of in situ image data, in situ diffraction pattern data, and subject data, wherein the in situ diffraction pattern data is acquired from the tissue diffractometer, wherein the at least one computer processor is configured to analyze the human tissue data and to produce the diagnostic indicator; and
    a communication interface configured to allow the at least one computer processor to send and receive information relevant to the diagnostic indicator,
    wherein the at least one computer processor uses the communication interface to receive the human tissue data from the tissue diffractometer and transmit the human tissue data to the computer database over the network.

2. The system of claim 1, further comprising the tissue diffractometer operatively coupled to the computer database over the network.

3. The system of claim 2,
    wherein the at least one computer processor uses the communication interface to process the human tissue data using a data analytics algorithm that provides the diagnostic indicator of the human tissue.

4. The system of claim 2, wherein the tissue diffractometer is configured for acquisition and transfer of data from the data group consisting of the in situ image data, the in situ diffraction pattern data, and the subject data, to the computer database over the network.

5. The system of claim 4, wherein the at least one computer processor is configured to:
    i. receive the data from the data group;
    ii. transmit the data from the data group; and
    iii. process the data from the data group for a human subject using a data analytics algorithm that provides the diagnostic indicator for the human tissue.

6. The system of claim 2, further comprising a user interface that allows a human subject or their healthcare provider to upload the subject data from the data group to the computer database in exchange for processing of the subject data to receive the diagnostic indicator for the human tissue.

7. The system of claim 6, wherein the user interface is further configured to allow the human subject or their healthcare provider to make payments or upload a human subject's signed consent form.

8. The system of claim 2, comprising at least two of the tissue diffractometers, each being located in different geographic locations.

9. The system of claim 2, wherein the tissue diffractometer includes a data encryption device that includes a global positioning system (GPS) positioning sensor and generates encrypted in situ image data, encrypted in situ diffraction pattern data, encrypted subject data, or any combination thereof, wherein the encrypted in situ image data, encrypted in situ diffraction pattern data, encrypted subject data, or any combination thereof that is transferred to the computer database tracks changes in location of the tissue diffractometer.

10. The system of claim 9, wherein the tissue diffractometer is configured to perform small angle X-ray scattering (SAXS) measurements.

11. The system of claim 10, wherein the tissue diffractometer is configured to perform wide angle X-ray scattering (WAXS) measurements.

12. The system of claim 11, wherein the tissue diffractometer is further configured to perform mammography.

13. The system of claim 10, wherein a set of target coordinates for directing an X-ray beam are determined from a mammogram.

14. The system of claim 9, wherein the in situ image data, the in situ diffraction pattern data, the subject data, or any combination thereof transferred to the computer database is depersonalized prior to transfer.

15. The system of claim 14, wherein a key for mapping depersonalized in situ image data, depersonalized in situ diffraction pattern data, depersonalized subject data, or any combination thereof stored in the computer database to a human subject is stored in a local institutional database or in personal files of the human subject.

16. The system of claim 2, wherein the computer database resides on a central server.

17. The system of claim 2, wherein the computer database resides in a cloud.

18. The system of claim 3, wherein the data analytics algorithm comprises a statistical analysis of diffraction pattern data or a function thereof.

19. The system of claim 18, wherein the statistical analysis comprises determination of a pair-wise distance distribution function, determination of a Patterson function, a calculation of a Porod invariant, a cluster analysis, a dispersion analysis, determination of one or more molecular structural periodicities, or any combination thereof.

20. The system of claim 19, wherein the statistical analysis comprises a determination of a structural periodicity of collagen.

21. The system of claim 19, wherein the statistical analysis comprises a determination of a structural periodicity of one or more lipids.

22. The system of claim 19, wherein the statistical analysis comprises a determination of a structural periodicity of a tissue.

23. The system of claim 18, wherein the data analytics algorithm comprises a machine learning algorithm.

24. The system of claim 23, wherein the machine learning algorithm comprises a supervised learning algorithm, an unsupervised learning algorithm, a semi-supervised learning algorithm, a reinforcement learning algorithm, a deep learning algorithm, or any combination thereof.

25. The system of claim 24, wherein the machine learning algorithm is the deep learning algorithm.

26. The system of claim 25, wherein the deep learning algorithm is a convolutional neural network, a recurrent neural network, or a recurrent convolutional neural network.

27. The system of claim 23, wherein the machine learning algorithm is trained using a training dataset comprising image data, diffraction pattern data, the subject data, or any combination thereof stored in the computer database for a specific pathology or physiological norm group.

28. The system of claim 27, wherein the training dataset is updated as new in situ image data, new in situ diffraction pattern data, new subject data, or any combination thereof and is uploaded to the computer database.

29. The system of claim 1, wherein the subject data comprises a human subject's age, sex, ancestry data, genetic data, behavioral data, or any combination thereof.

30. The system of claim 29, wherein the diagnostic indicator for the human tissue comprises an indicator of a likelihood that the human subject has cancer.

31. The system of claim 30, wherein the indicator of the likelihood that the human subject has cancer is an indicator of the likelihood that the human subject has breast cancer.

32. The system of claim 29, wherein the diagnostic indicator for the human tissue comprises a diagnosis that the human subject has cancer.

33. The system of claim 32, wherein the diagnosis that the human subject has cancer is a diagnosis that the human subject has breast cancer.

\* \* \* \* \*